United States Patent [19]

Mishima et al.

[11] 4,199,519

[45] Apr. 22, 1980

[54] HIGHER POLYALKENYL FATTY ACIDS AND ESTERS

[75] Inventors: Hiroshi Mishima; Akira Ogiso; Shinsaku Kobayashi, all of Tokyo, Japan

[73] Assignee: Sankyo Company Limited, Tokyo, Japan

[21] Appl. No.: 938,356

[22] Filed: Aug. 31, 1978

Related U.S. Application Data

[62] Division of Ser. No. 788,699, Apr. 18, 1977, Pat. No. 4,151,357.

[30] Foreign Application Priority Data

Apr. 24, 1976 [JP] Japan .................................. 51-46937

[51] Int. Cl.$^2$ ...................... C07C 57/02; C07C 69/52
[52] U.S. Cl. .................................. 260/413; 560/183; 544/377; 544/401; 424/250
[58] Field of Search ................. 544/377, 401; 260/413; 560/183

[56] References Cited

U.S. PATENT DOCUMENTS 4,151,357  4/1979  Mishima et al. ..................... 544/386

*Primary Examiner*—Jose Tovar
*Attorney, Agent, or Firm*—Frishauf, Holtz, Goodman & Woodward

[57] ABSTRACT

Polyprenyl derivatives having the formula

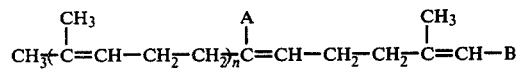

[wherein A and B individually represent a group of the formula —CH$_2$OR$^1$ (wherein R$^1$ is hydrogen atom, an alkyl group having an intervening hetero atom in the carbon chain, carboxyl group on its salt or an aliphatic acyl group optionally having an intervening hetero atom in the carbon chain, an aromatic acyl group, a heterocyclic acyl group, an araliphatic acyl group, a heterocyclic aliphatic acyl group or a radical of an inorganic acid or its salt) or where one of A and B represents the group —CH$_2$OR$^1$, the other represents a group of the formula —COOR$^2$ (wherein R$^2$ represents hydrogen atom, a metal atom capable of forming a salt, an organic base or an akyl group), a group of the formula

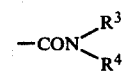

or a group of the formula

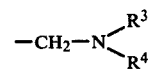

(wherein R$^3$ and R$^4$ may be the same or different and each represents hydrogen atom, an alkyl group optionally having a heterocyclic substituent, an aryl group or an aralkyl group or R$^3$ and R$^4$ may jointly form a ring optionally containing other hetero ring atom) and n is an integer of 0 to 4 inclusive, provided that when both A and B are the group —CH$_2$OR$^1$, either of the R$^1$ represents an alkyl group having an intervening hetero atom, carboxyl group or its salt, an aliphatic acyl group having an intervening hetero atom in the carbon chain, a heterocyclic acyl group, a heterocyclic aliphatic acyl group or a radical of an inorganic acid or its salt]. These derivatives are useful as medicines for treating peptic ulcer.

3 Claims, No Drawings

HIGHER POLYALKENYL FATTY ACIDS AND ESTERS

This is a division, of application Ser. No. 788,699, filed Apr. 18, 1977 now U.S. Pat. No. 4,151,357 issued Apr. 24, 1979.

This invention relates to novel polyprenyl derivatives. More particularly, it is concerned with polyprenyl derivatives having the general formula

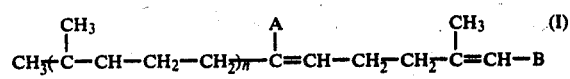

[wherein A and B individually represent a group of the formula —$CH_2OR^1$ (wherein $R^1$ is hydrogen atom, an alkyl group having an intervening hetero atom in the carbon chain, carboxyl group or its salt or an aliphatic acyl group optionally having an intervening hetero atom in the carbon chain, an aromatic acyl group, a heterocyclic acyl group, an aralphatic acyl group, a heterocyclic aliphatic acyl group or a radical of an inorganic acid or its salt) or where one of A and B represents the group —$CH_2OR^1$, the other represents a group of the formula —$COOR^2$ (wherein $R^2$ represents hydrogen atom, a metal atom capable of forming a salt, an organic base or an alkyl group), a group of the formula

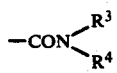

or a group of the formula

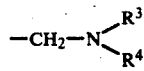

(wherein $R^3$ and $R^4$ may be the same or different and each represents hydrogen atom, an alkyl group optionally having a heterocyclic substituent, an aryl group or an aralkyl group or $R^3$ and $R^4$ may jointly form a ring optionally containing other hetero ring atom) and n is an integer of 0 to 4 inclusive, provided that when both A and B are the group —$CH_2OR^1$, either of the $R^1$ represents an alkyl group having an intervening hetero atom, carboxyl group or its salt, an aliphatic acyl group having an intervening hetero atom in the carbon chain, a heterocyclic acyl group, a heterocyclic aliphatic acyl group or a radical of an inorganic acid or its salt].

The polyprenyl derivatives (I) according to this invention are of value as medicines for treating peptic ulcer.

In the above general formula (I), A and B are both a group of the formula —$CH_2OR^1$ or, in case where one of them is the group of the formula —$CH_2OR^1$, the other is a group of the formula —$CO_2R^2$, a group of the formula —$CONR^3R^4$ or a group of the formula —$CH_2NR^3R^4$. $R^1$ is, for example, hydrogen atom, an alkyl group of 1 to 8 carbon atoms such as methyl, ethyl, n-propyl, isopropyl, n-butyl, isobutyl, n-pentyl, hexyl, heptyl, octyl; an alkyl group of 3 to 6 carbon atoms and having an intervening hetero atom in the carbon chain such as dimethylaminoethyl, diethylaminoethyl, methylthioethyl, n-propylthioethyl; an alkanoyl group of 2 to 8 carbon atoms such as acetyl, propionyl, butyryl, isobutyryl, valeryl, caproyl, heptanoyl, octanoyl; a carboxyalkanoyl group of 2 to 7 carbon atoms such as oxalate, malonate, succinate, glutarate, adipate, pimelate and their salts with an organic base such as pyridine, an alkali-metal such as sodium, potassium, an alkaline earth metal such as calcium, barium, aluminum and bismuth; an aliphatic acyl group of 3 to 8 carbon atoms and having an intervening hetero atom in the carbon chain such as dimethylaminoacetyl, bromotriethylammonium acetyl, methylthioacetyl, n-butylthioacetyl; an aromatic acyl group such as benzoyl, anisoyl; a heterocyclic acyl group such as nicotinoyl, isonicotinoyl, pyrrolylcarbonyl, indolylcarbonyl, pyrrolidinylcarbonyl, piperizinocarbonyl, thienylcarbonyl, furylcarbonyl, isoxazolylcarbonyl, thiazolylcarbonyl; an araliphatic acyl group having a carbon chain of 2 to 3 carbon atoms such as phenylacetyl, phenylpropionyl; a heterocyclic aliphatic acyl group having a carbon chain of 2 to 4 carbon atoms such as thienylacetyl, furylacetyl, pyridylacetyl, pyrrolylacetyl, pyrrolidinylacetyl, piperizinoacetyl, thiazolylthioacetyl; an inorganic acid residue such as sulfate, phosphate and their salts with an organic base such as pyridine, diethanolamine, a alkali metal such as sodium, potassium, or alkaline earth metal such as calcium, barium, aluminium or bismuth. $R^2$ is, for example, hydrogen atom, an alkali metal such as sodium, potassium, an alkaline earth metal such as calcium, barium, a metal atom capable of forming a salt such as aluminum, bismuth, an organic base capable of forming a salt such as pyridine, diethanolamine, an alkyl group of 1 to 8 carbon atoms such as methyl, ethyl, n-propyl, isopropyl, n-butyl, isobutyl, n-pentyl, hexyl, heptyl, octyl. $R^3$ and $R^4$ may be the same or different and each represents hydrogen atom, an alkyl group of 1 to 8 carbon atoms such as methyl, ethyl, n-propyl, isopropyl, n-butyl, isobutyl, n-pentyl, hexyl, heptyl, octyl, an alkyl group of 1 to 4 carbon atoms and having a heterocyclic substituent such as 1-pyrrolidinylmethyl, 1-pyrrolidinylethyl, 1-pyrrolidinylpropyl, 1-pyrrolidinylbutyl, piperidinomethyl, piperidinoethyl, piperidinobutyl, morpholinomethyl, morpholinoethyl, morpholinopropyl, morpholinobutyl, 4-phenyl-1-piperazinylmethyl, 4-(p-methoxyphenyl)-1-piperazinylethyl, 4-(2-hydroxyethyl)-1-piperazinylpropyl, 4-methyl-1-piperazinylbutyl, an aryl group such as phenyl which optionally has as a substituent alkyl of 1 to 2 carbon atoms such as methyl, ethyl, alkoxy of 1 to 3 carbon atoms such as methoxy, ethoxy, n-propoxy, isopropoxy or halogen such as chlorine, bromine, fluorine in the aromatic ring, an aralkyl group such as benzyl, phenethyl, phenylpropyl which has a carbon chain of 1 to 3 carbon atoms and optionally as a substituent alkyl of 1 to 2 carbon atoms such as methyl, ethyl, alkoxy of 1 to 3 carbon atoms such as methoxy, ethoxy, n-propoxy, isopropoxy or halogen such as chlorine, bromine, fluorine, in the aromatic ring or a cyclic group which $R^3$ and $R^4$ jointly form such as 1-pyrrolidinyl, piperidino, morpholino, 4-methyl-1-piperazinyl, 4-phenyl-1-piperazinyl, 4-(p-methoxyphenyl)-1-piperazinyl,4-(3,4-methylenedioxybenzyl)-1-piperazinyl,4-(2-hydroxyethyl)-1-piperazinyl,2-imidazolin-1-yl, 1-indolinyl.

As a preferable group of the compounds of the above general formula (I) can be mentioned those compounds of the formula (I) wherein A and B individually represent a group of the formula —$CH_2OR^1$ (wherein $R^1$ represent hydrogen atom, an alkyl group having 1 to 4 carbon atoms, an alkyl group having an intervening hetero atom in the carbon chain and 3 to 6 carbon atoms, an aliphatic acyl group having 2 to 8 carbon atoms, an aliphatic acyl group having carboxyl group or its salt can 2 to 7 carbon atoms, an aliphatic acyl group having an intervening hetero atom in the carbon chain and 3 to 8 carbon atoms, an aromatic acyl group, a heterocyclic acyl group containing 1 to 2 hetero atoms, a heterocyclic acyl group having a heterocyclic group containing 1 to 2 hetero atoms and the carbon chain of 2 to 4 carbon atoms or sulfuric acid radical or its salt), or where one of A and B is the group —$CH_2OR^1$, the other represents a group of the formula -$COOR^2$ (wherein $R^2$ represents hydrogen atom, a metal atom or organic base capable of forming a salt or an alkyl group having 1 to 4 carbon atoms), a group of the formula

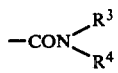

or a group of the formula

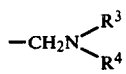

(wherein $R^3$ and $R^4$ may be the same or different and each represents hydrogen atom, an alkyl group having 1 to 8 carbon atoms, an alkyl group having a heterocyclic group containing 1 to 2 hetero atoms and 1 to 4 carbon atoms or $R^3$ and $R^4$ may jointly form a 5- or 6-membered ring optionally having one other hetero atom) and n is an integer of 0 to 2 inclusive.

In the compounds having the above general formula (I) of this invention, there can be present a number of geometrical isomers due to configuration of the double bond. This configuration is expressed according to the E, Z designation prescribed in the nomenclature proposed by IUPAC, which is shown in The Journal of Organic Chemistry, 35, 2849 (1970). In the general formula (I) as shown herein, all of these isomers and mixtures thereof are presented in a single formula, but it should not be construed to limit the scope of this invention.

We have made for many years studies on polyprenyl derivatives having a pharmacological activity, some of which was previously disclosed and claimed in our co-pending U.S. Pat. application Ser. No. 633,097 filed on Nov. 18, 1975, and now U.S. Pat. No. 4,059,641. As a result of our further studies on various homologous compounds and derivatives of our previously developed polyprenyl compounds, it has been found that the novel polyprenyl compound having the above general formula (I) is highly effective for treatment of peptic ulcer and thus the present invention has been completed upon this finding.

It is, accordingly, a primary object of this invention to provide a new group of the polyprenyl derivatives having the above formula (I) which exhibits potent anti-ulcer activity.

Activities of the present polyprenyl derivatives suppressing the ulcer are seen from the following comparative pharmacological tests.

(1) Anti-reserpine ulcer activity

Test procedures

The test was carried out in accordance with the method described by C. Blackmann, D. S. Campion and F. N. Fastier in British Journal of Pharmacology and Chemotherapy, vol. 14, 112 (1959), which is as follows:

The test compound was intraperitoneally administered to male mice (ddY strains, body weight: 28–33 g), and, 30 minutes later, reserpine was subcutaneously administered in the dose of 10 mg/kg. After 18 hours from the reserpine administration, the animal was sacrificed, and the stomach was isolated. This stomach was inflated with 2 ml of 0.5% formalin and was fixed. Then, the stomach was opened by cutting along the greater curvature, and the ulcer area[1] was measured with a stereoscopic microscope. The ulcer areas of the treated group and the control group were compared, and the inhibitory ratios were calculated.

[1] ulcer area (mm$^2$): sum of each ulcer area (longitude×latitude)

(2) Anti-stress ulcer activity

Test procedures

The test was carried out in accordance with the method described by S. Yano, M. Harada in The Japanese Journal of Pharmacology, vol. 23,57 (1973), which is as, follows:

Male mice (ddY strains, body weight: 28–32 g) were placed under restraint in a stress cage and immersed vertically in the water bath kept at 25°±1° C. to the height of the xiphoid of the animal. After restraint-immersion for 8 hours, the animals were sacrificed. The stomach was fixed with formalin and measured in its ulcer index [2]. The ulcer indices of the treated group and the control group were compared, and the inhibitory ratios were calculated. The test compound was orally administered immediately before the restraint-immersion.

[2] ulcer index (mm): sum of the length of each linear ulcer

Test results

The anti-reserpine ulcer activity shown when the test compound was intraperitoneally administered at 0.3 m mole/kg and the anti-stress ulcer activity shown when the test compound was orally administered at 1 m mole/kg are set out in Tables 1 and 2.

Table 1

| Anti-reserpine ulcer activity | | |
|---|---|---|
| Test compound | Number of animal | Inhibitory ratio (%) |
| Compound 1 | 5 | 41 |
| Compound 2 | 5 | 49 |
| Compound 3 | 5 | 50 |
| Compound 4 | 5 | 45 |
| Compound 6 | 5 | 53 |
| Compound 7 | 5 | 82 |
| Compound 8 | 5 | 49 |
| Compound 9 | 5 | 91 |
| Compound 10 | 5 | 75 |
| Compound 11 | 5 | 55 |
| Compound 12 | 5 | 74 |
| Compound 13 | 5 | 84 |
| Compound 14 | 5 | 57 |
| Compound 15 | 5 | 85 |
| Compound 16 | 5 | 68 |
| Compound 17 | 5 | 72 |
| Compound 18 | 5 | 46 |
| Compound 19 | 5 | 46 |
| Compound 20 | 5 | 53 |
| Compound 21 | 5 | 98 |
| Compound 22 | 5 | 74 |
| Compound 23 | 5 | 71 |
| Compound 24 | 5 | 46 |
| Compound 25 | 5 | 60 |
| Gefarnate | 5 | 10 |

Table 2

| Test compound | Anti-stress ulcer activity | |
|---|---|---|
| | Number of animal | Inhibitory ratio (%) |
| Compound 1 | 10 | 90 |
| Compound 2 | 10 | 100 |
| Compound 3 | 10 | 80 |
| Compound 4 | 5 | 58 |
| Compound 5 | 5 | 84 |
| Compound 8 | 5 | 84 |
| Compound 11 | 5 | 73 |
| Compound 12 | 5 | 89 |
| Compound 13 | 5 | 67 |
| Compound 14 | 5 | 95 |
| Compound 15 | 5 | 67 |
| Compound 16 | 5 | 85 |
| Compound 17 | 5 | 68 |
| Compound 18 | 5 | 90 |
| Compound 19 | 5 | 82 |
| Compound 23 | 10 | 50 |
| Compound 25 | 10 | 52 |
| Compound 26 | 5 | 77 |
| Gefarnate | 10 | 52 |

Compound 1:
 (E,Z,E) and (E,E,E)-7-Hydroxymethyl-3,11,15-trimethyl-2,6,10,14-hexadecatetraenoic acid Compound 2:
 (E,Z,E) and (E,E,E)-7-Carboxy-3,11,15-trimethyl-2,6,10,14-hexadecatetraen-1-ol Compound 3:
 (E,Z,E) and (E,E,E)-7-Ethoxycarbonyl-3,11,15-trimethyl-2,6,10,14-hexadecatetraen-1-ol Compound 4:
 (E,E) and (Z,E)-N,N-Diethyl-8-hydroxy-3,7-dimethyl-2,6-octadienamide Compound 5:
 4-[(E,E) and (Z,E)-8-Hydroxy-3,7-dimethyl-2,6-octadienoyl] morpholine Compound 6:
 (E,Z,E) and (E,E,E)-N-Benzyl-7-hydroxymethyl-3,11,15-trimethyl-2,6,10,14-hexadecatetraenamide Compound 7:
 (E,Z,E),(E,E,E),(Z,Z,E) and (Z,E,E)-N-Ethyl-7-hydroxymethyl-3,11,15-trimethyl-2,6,10,14-hexadecatetraenamide Compound 8:
 (E,Z,E),(E,E,E),(Z,Z,E) and (Z,E,E)-N-[2-(1-pyrrolidinyl)ethyl]-7-Hydroxymethyl-3,11,15-trimethyl-2,6,10,14-hexadecatetraenamide Compound 9:
 (E,Z,E) and (E,E,E)-N-(p-Methylphenyl)-7-acetoxymethyl-3,11,15-trimethyl-2,6,10,14-hexadecatetraenamide Compound 10:
 1-[(E,Z,E), (E,E,E), (Z,Z,E) and (Z,E,E)-7-Hydroxymethyl-3,11,15-trimethyl-2,6,10,14-hexadecatetraenoyl]pyrrolidine Compound 11:
 4-[(E,E,E)-7-Hydroxymethyl-3,11,15-trimethyl-2,6,10,14-hexadecatetraenoyl] morpholine Compound 12:
 1-[(E,Z,E),(E,E,E),(Z,Z,E) and (Z,E,E)-7-Hydroxymethyl 3,11,15-trimethyl-2,6,10,14-hexadecatetraenoyl]-4-(2-hydroxyethyl)piperazine Compound 13:
 (E,Z,E) and (E,E,E)-N,N-Diethyl-7-acetoxymethyl-3,11,15-trimethyl-2,6,10,14-hexadecatetraenamide Compound 14:
 1-[(E,E) and (E,Z)-8-Hydroxy-3,7-dimethyl-2,6-octadien-1-yl]-4-(3,4-methylenedioxybenzyl)piperazine Compound 15:
 1-[(E,Z,E) and (E,E,E)-7-Hydroxymethyl-3,11,15-trimethyl-2,6,10,14-hexadecatetraen-1-yl]-4-phenylpiperazine Compound 16:
 1-[(E,Z,E) and (E,E,E)-7-Hydroxymethyl-3,11,15-trimethyl-2,6,10,14-hexadecatetraen-1-yl]-4-(3,4-methylenedioxybenzyl) piperazine Compound 17:
 (E,Z,E) and (E,E,E)-7-Isobutylaminomethyl-3,11,15-trimethyl-2,6,10,14-hexadecatetraen-1-ol Compound 18:
 (E,Z,E) and (E,E,E)-7-(3-Piperizinopropylaminomethyl)-3,11,15-trimethyl-2,6,10,14-hexadecatetraen-1-ol Compound 19:
 (E,Z), (E,E), (Z,Z) and (Z,E)-7-Octylaminomethyl-3,11-dimethyl-2,6,10-dodecatrien-1-ol Compound 20:
 (E,E)-8-Acetoxy-2,6-dimethyl-2,6-octadienyl-1-ol sulfate sodium salt Compound 21:
 (E,Z,E) and (E,E,E)-7-Hydroxymethyl-3,11,15-trimethyl-2,6,10,14-hexadecatetraen-1-ol disulfate pyridine salt Compound 22:
 (E,Z,E) and (E,E,E)-7-Hydroxymethyl-3,11,15-trimethyl-2,6,10,14-hexadecatetraen-1-ol disulfate sodium salt Compound 23:
 (E,Z,E) and (E,E,E)-7-Hydroxymethyl-3,11,15-trimethyl-2,6,10,14-hexadecatetraen-1-Bl disuccinate sodium salt Compound 24:
 (E,Z,E) and (E,E,E)-7-Hydroxymethyl-3,11,15-trimethyl-2,6,10,14-hexadecatetraen-1-ol bis-2-thienyl acetate Compound 25:
 (E,Z,E) and (E,E,E)-7-Hydroxymethyl-3,11,15-trimethyl-2,6,10,14-hexadecatetraen-1-ol diisonicotinate Compound 26:
 (E,Z,E) and (E,E,E)-7-Hydroxymethyl-3,11,15-trimethyl-2,6,10,14-hexadecatetraen-1-ol bis-2-thiazolin-2-yl thioacetate As seen from the Tables, the compounds of the aforementioned formula (I) are of values as medicines for treating peptic ulcer.

These compounds may be administered parenterally through subcutaneous or intramuscular injection, or orally in the form of tablets, capsules, granules, powders and the like. The dosage to be administered may vary depending upon condition, age, weight, administration procedure and the like, and a dosage of about 10–1000 mg per day is usually given to an adult at once or in the form of 2–4 divided portions.

Representatives of the compound having the above general formula (I) are recited below, but they are not limiting the scope of the present compounds.

(1) N,N-diethyl-8-hydroxy-3,7-dimethyl-2,6-octadienamide and the corresponding acetate and benzoate (2) 4-(8-hydroxy-3,7-dimethyl-2,6-octadienoyl) morpholine and the corresponding acetate and benzoate (3) 1-(8-hydroxy-3,7-dimethyl-2,6-octadienoyl)-4-(3,4-methylenedioxybenzyl)piperazine and the corresponding acetae and benzoate
(4) 1-(7-hydroxymethyl-3,11-dimethyl-2,6,10-dodecatrienoyl) piperidine and the corresponding acetate and benzoate
(5) N-(1-pyrrolidinylmethyl)-7-hydroxymethyl-3,11-dimethyl-2,6,10-dodecatrienamide and the corresponding acetate and benzoate
(6) 7-hydroxymethyl-3,11,15-trimethyl-2,6,10,14-hexadecatetraenoic acid and the corresponding methyl and ethyl esters
(7) 7-hydroxymethyl-3,11,15-trimethyl-2,6,10,14-hexadecatetraenamide and the corresponding acetate and benzoate
(8) N-benzyl-7-hydroxymethyl-3,11,15-trimethyl-2,6,10,14-hexadecaetraenamide and the corresponding acetate and benzoate
(9) N-ethyl-7-hydroxymethyl-3,11,15-trimethyl-2,6,10,14-hexadecatetraenamide and the corresponding acetate and benzoate
(10) N-[2-(1-pyrrolidinyl)ethyl]-7-hydroxymethyl-3,11,15-trimethyl-2,6,10,14-hexadecatetraenamide and the corresponding acetate and benzoate
(11) N-(p-methylphenyl)-7-hydroxymethyl-3,11,15-trimethyl-2,6,10,14-hexadecatetraenamide and the corresponding acetate and benzoate
(12) 1-(7-hydroxymethyl-3,11,15-trimethyl-2,6,10,14-hexadecatetraenoyl)pyrrolidine and the corresponding acetate and benzoate
(13) 4-(7-hydroxymethyl-3,11,15-trimethyl-2,6,10,14-hexadecatetraenoyl)morpholine and the corresponding acetate and benzoate
(14) 1-(7-hydroxymethyl-3,11,15-trimethyl-2,6,10,14-hexadecatetraenoyl)-4-(2-hydroxyethyl)piperazine and the corresponding mono- or diacetate and mono- or dibenzoate
(15) 1-(7-hydroxymethyl-3,11,15-trimethyl-2,6,10,14-hexadecatetraenoyl)-4-phenylpiperazine and the corresponding acetate and benzoate
(16) N,N-diethyl-7-hydroxymethyl-3,11,15-trimethyl-2,6,10,14-hexadecatetraenamide and the corresponding acetate and benzoate
(17) 1-(7-hydroxymethyl-3,11,15-trimethyl-2,6,10,14-hexadecatetraenoyl)-4-(3,4-methylenedioxybenzyl) piperazine and the corresponding acetate and benzoate
(18) 7-dimethylcarbamoyl-3,11-dimethyl-2,6,10-dodecatrien-1-ol and the corresponding acetate and benzoate
(19) 7-morpholinocarbonyl-3,11-dimethyl-2,6,10-dodecatrien-1-ol and the corresponding acetate and benzoate
(20) 7-ethoxycarbonyl-3,11,15-trimethyl-2,6,10,14-hexadecatetraen-1-ol and the corresponding acetate and benzoate
(21) 7-carboxy-3,11,15-trimethyl-2,6,10,14-hexadecatetraen-1-ol and the corresponding methyl and ethyl esters
(22) 7-benzylcarbamoyl-3,11,15-trimethyl-2,6,10,14-hexadecatetraen-1-ol and the corresponding acetate and benzoate
(23) 1-(8-hydroxy-2,6-dimethyl-2,6-octadienoyl)-4-(2-hydroxyethyl)piperazine and the corresponding diacetate and dibenzoate
(24) N-[2-(1-pyrrolidinyl)ethyl]-8-hydroxy-2,6-dimethyl-2,6-octadienamide and the corresponding acetate and benzoate
(25) 1-(8-hydroxy-3,7-dimethyl-2,6-octadien-1-yl)-4-(3,4-methylenedioxybenzyl)piperazine and the corresponding acetate and benzoate
(26) 1-(8-hydroxy-3,7-dimethyl-2,6-octadien-1-yl)-4-(2-hydroxyethyl)piperazine and the corresponding monoacetate and mono- or dibenzoate
(27) 1-(8-hydroxy-2,6-dimethyl-2,6-octadien-1-yl)indoline and the corresponding acetate and benzoate
(28) 4-(8-hydroxy-2,6-dimethyl-2,6-octadien-1-yl) morpholine and the corresponding acetate and benzoate
(29) 1-(7-hydroxymethyl-3,11-dimethyl-2,6,10-dodecatrien-1-yl)imidazoline-(2) and the corresponding acetate and benzoate
(30) 1-(7-hydroxymethyl-3,11-dimethyl-2,6,10-dodecatrien-1-yl)-4-(p-methoxyphenyl)piperazine and the corresponding acetate and benzoate
(31) 7-octylaminomethyl-3,11-dimethyl-2,6,10-dodecatrien-1-ol and the corresponding O-acetate and O-benzoate
(32) 7-diisopropylaminomethyl-3,11-dimethyl-2,6,10-dodecatrien-1-ol and the corresponding acetate and benzoate
(33) 7-(2-piperidinoethylaminomethyl)-3,11-dimethyl-2,6,10-dodecatrien-1-ol and the corresponding O-acetate and O-benzoate
(34) 1-(7-hydroxymethyl-3,11,15-trimethyl-2,6,10,14-hexadecatetraen-1-yl)-4-phenyl piperazine and the corresponding acetate and benzoate
(35) 1-(7-hydroxymethyl-3,11,15-trimethyl-2,6,10,14-hexadecatetraen-1-yl)-4-(3,4-methylenedioxybenzyl) piperazine and the corresponding acetate and benzoate
(36) 7-isobutylaminomethyl-3,11,15-trimethyl-2,6,10,14-hexadecatetraen-1-ol and the corresponding O-acetate and O-benzoate
(37) 7-(3-piperidinopropylaminomethyl)-3,11,15-trimethyl-2,6,10,14-hexadecatetraen-1-ol and the corresponding O-acetate and O-benzoate
(38) 8-acetoxy-2,6-dimethyl-2,6-octadienyl-1-ol sulfate and the corresponding sodium salt and pyridine salt
(39) 7-hydroxymethyl-3,11-dimethyl-2,6,10-dodecatrien-1-ol disulfate and the corresponding sodium salt and pyridine salt
(40) 7-hydroxymethyl-3,11-dimethyl-2,6,10-dodecatrien-1-ol disuccinate and the corresponding sodium salt
(41) 7-hydroxymethyl-3,11,15-trimethyl-2,6,10,14-hexadecatetraen-1-ol bis-N,N-diethylaminoethyl ether
(42) 7-hydroxymethyl-3,11,15-trimethyl-2,6,10,14-hexadecatetraen-1-ol disulfate and the corresponding sodium salt and pyridine salt
(43) 7-hydroxymethyl-3,11,15-trimethyl-2,6,10,14-hexadecatetraen-1-ol disuccinate and the corresponding sodium salt
(44) 7-hydroxymethyl-3,11,15-trimethyl-2,6,10,14-hexadecatetraen-1-ol bis-n-butylthioacetate
(45) 7-hydroxymethyl-3,11,15-trimethyl-2,6,10,14-hexadecatetraen-1-ol bis-bromotrimethyl ammonium acetate
(46) 7-hydroxymethyl-3,11,15-trimethyl-2,6,10,14-hexadecatetraen-1-ol bis-2-thienylacetate
(47) 7-hydroxymethyl-3,11,15-trimethyl-2,6,10,14-hexadecatetraen-1-ol diisonicotinate
(48) 7-hydroxymethyl-3,11,15-trimethyl-2,6,10,14-hexadecatetraen-1-ol bis-2-thiazolin-2-yl acetate The above exemplified compounds are present as a number of geometrical isomers due to configuration of the double bonds. Therefore, the above exemplified compounds may be obtained in the form of a number of isomers set out below and mixtures of these isomers.

Compounds (1), (2), (3), (4), (5), (18), (19), (23), (24), (25), (26), (27), (28), (29), (30), (31), (32), (33), (38), (39) and (40): (E,Z), (E,E), (Z,Z) and (Z,E)

Compounds (6), (7), (8), (9), (10), (11), (12), (13), (14), (15), (16), (17), (20), (21), (22), (34), (35), (36), (37), (41), (42), (43), (44), (45), (46), (47) and (48): (E,Z,E), (E,E,E), (Z,Z,E) and (Z,E,E) isomers.

In accordance with this invention, the compound having the above general formula (I) can be prepared by the following processes.

Process 1

The compound of the above general formula (I) wherein A is hydroxymethyl group or an acyloxymethyl group and B is carboxyl group, namely, the compound of the general formula

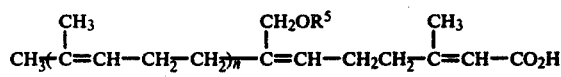
(II)

(wherein $R^5$ is hydrogen atom or an aliphatic or aromatic acyl group and n is 0–4) can be produced by reacting a compound of the general formula

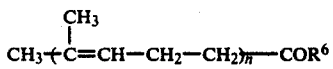
(III)

(wherein $R^6$ represents a protected hydroxymethyl group or a protected formyl group and n has the same meaning as above) with

(IV)

(wherein $R^7$ represents a hydrocarbyl residue such as phenyl, n-butyl and X represents a halogen atom such as bromine or iodine) in the presence of a base to produce a compound of the general formula

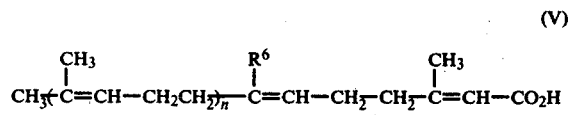
(V)

(wherein $R^6$ and n have the same meanings as above) and removing the protecting group from the protected hydroxy group of the so obtained compound on the protecting group from the protected formyl group thereof followed by reduction of the free formyl group.

There is no particular limitation on the protecting group of the hydroxy group if the protecting group does not affect other portion of a compound upon subsequent conversion to hydrogen atom and examples of such a protecting group may be, for instance, a 5- or 6-membered cyclic group having oxygen or sulfur atom in the ring and optionally an alkoxy group as a substituent, e.g., 2-tetrahydrofuranyl, 2-tetrahydropyranyl, 2-tetrahydrothienyl, 2-tetrahydrothiopyranyl, and 4-methoxytetrahydropyran-4-yl; an alkoxy-lower alkyl group, e.g., methoxymethyl, ethoxymethyl, n-propoxymethyl, isopropoxymethyl, n-butoxymethyl, isobutoxymethyl, 1-ethoxyethyl, 1-ethoxypropyl, 1-methoxy-1-methylethyl; a tri-lower alkyl-silyl group, e.g., trimethylsilyl, triethylsilyl, tri-n-propylsilyl, triisopropylsilyl, tri-n-butylsilyl, triisobutylsilyl; and an aliphatic or aromatic acyl group, e.g., acetyl, propionyl, butyryl, isobutyryl and benzoyl. Particularly preferable are 2-tetrahydropyranyl, methoxymethyl, trimethylsilyl, acetyl and benzoyl. In this stage, the compounds having an aliphatic or aromatic acyl group may be directed to the end product. Also, there is no particular limitation on the protective group for formyl group so far as it may form an acetal linkage and preferable are, for example, those capable of forming dimethoxymethyl, diethoxymethyl, ethylenedioxymethyl and the like.

In the present process, the condensation reaction involving the compound of the formula (III) and the compound of the formula (IV) for preparing the compound of the formula (V) is carried out in the presence of a base and a solvent. There is no specific limitation on the base employed, so far as it belongs to the base adopted for the general Wittig reaction. Preferable are an alkali metal hydride compound such as sodium hydride, an alkali metal amide compound such as sodium amide, potassium amide and an alkali metal alcoholate compound such as potassium tert-butoxide. There likewise is no specific limitation on the solvent employed, so far as it does not participate in the reaction. Preferred are an ether such as ethyl ether, tetrahydrofuran, dioxane and 1,2-dimethoxyethane, an aromatic hydrocarbon such as benzene, toluene, a dialkyl aliphatic amine such as dimethylformamide, dimethylacetamide, dimethyl sulfoxide. There is no particular limitation on the reaction temperature, but it is preferably about 0° C.-60° C. Further, the reaction is preferably carried out in a stream of an inert gas such as nitrogen, helium and argon. Most preferred procedures for this reaction is as follows: The compound of the above general formula (III), that of the general formula (IV) and the base such as sodium hydride are added to the organic solvent such as dimethyl sulfoxide under an inert gas stream such as argon and then the mixture was heated to 50° C.-55° C. The reaction period may vary mainly depending upon the sort of the base employed and the reaction temperature, but it usually is between 2 and 10 hours.

After completion of the reaction, the desired compound of the aforementioned general formula (V) can be recovered from the reaction mixture in the conventional manner. For instance, after completion of the reaction, the reaction mixture is added to ice-water, neutralized with hydrochloric acid or acetic acid and extracted with an organic solvent such as n-hexane. The organic solvent layer is washed and dried. Upon evaporation of the solvent, the desired compound is obtained.

Then, the reaction for removing the protecting group of the hydroxy group from the compound of the above general formula (V) may be chosen depending upon the sort of the protecting group.

In case, for instance, the protecting group for the hydroxy is a heterocyclic group such as 2-tetrahydropyranyl or an alkoxyalkyl group such as methoxymethyl, the reaction is easily carried out by bringing the compound (V) into contact with an acid. Preferred acids are an organic acid such as formic acid, acetic acid, propionic acid and p-toluenesulfonic acid and an inorganic acid such as hydrochloric acid and sulfuric acid. The reaction is carried out in the presence or absence of a solvent. However, a solvent is preferably employed so as to carry out the reaction smoothly.

Preferred solvents are water, an alcohol such as methanol and ethanol, and a mixture of water and one of these alcohols. There is no specific limitation on the reaction temperature, but room temperature is preferably adopted. In case the protecting group for the hydroxyl group is a trialkylsilyl group such as trimethylsilyl, the reaction is easily carried out by brining the compound (V) into contact with water or an aqueous solution of an acid or a base. As the acid and base, there may be mentioned an acid such as an organic acid, e.g., formic acid, acetic acid and propionic acid, and an inorganic acid e.g., hydrochloric acid and sulfuric acid, a base such as hydroxide of an alkali metal and an alkaline earth metal, e.g., potassium hydroxide and calcium hydroxide, and carbonate of an alkali metal and an alkaline earth metal, e.g., potassium carbonate and calcium carbonate. There is no specific limitation on the reaction temperature, but in general, room temperature is preferably adopted. In case the protecting group for the hydroxy group is an acyl group such as acetyl or benzoyl, the reaction may be conducted according to the procedures for hydrolysis or alcoholysis of a conventional ester group in the presence of a base or acid, preferably by bringing the compound (V) into contact with the base. Preferred bases are hydroxides of an alkali metal and alkaline earth metal such as sodium hydroxide, potassium hydroxide and barium hydroxide, and carbonates of an alkali metal and an alkaline earth metal such as sodium carbonate, potassium carbonate and calcium carbonate. The present reaction is preferably carried out in water, an organic solvent such as an alcohol, e.g., methanol, ethanol and n-propanol, an ether e.g., tetrahydrofuran and dioxane, or a mixture of water and one of the said organic solvents. There is no specific limitation on the reaction temperature, but, in general, temperature around room temperature are preferably adopted.

The reaction time for the foresaid removal of the protecting groups may vary depending upon the type of the protecting group.

After completion of the reaction, the desired compound of the formula (II) can be obtained from the reaction mixture in the conventional manner. For instance, the reaction mixture is, after completion of the reaction, neutralized and extracted with an organic solvent such as ethyl ether. The organic solvent layer is washed and dried. Upon evaporation of the solvent, the desired compound is obtained.

The reaction for removing the protecting group from the formyl group of the compound having the formula (V) wherein the substitute $R^6$ is a protected formyl group can be performed in the manner as employed for hydrolysis of the usual acetal. Preferred is a method that involves bringing the compound (V) into contact with an acid. As a preferred acid to be used, there may be mentioned an organic acid such as formic acid, acetic acid and propionic acid and an inorganic acid such as hydrochloric acid and sulfuric acid. The present reaction is carried out in water or an aqueous organic solvent. Preferred aqueous organic solvents are an aqueous alcohol such as aqueous methanol and aqueous ethanol and an aqueous ether such as aqueous tetrahydrofuran and aqueous dioxane. There is no specific limitation on the reaction temperature, but, in general, temperatures around room temperature are preferably adopted.

After completion of the reaction, the compound obtained by removal of the protecting group of the formyl group can be recovered from the reaction mixture in the conventional manner. For instance, after completion of the reaction, the reaction mixture is extracted with an organic solvent such as n-Hexane. The organic solvent layer is washed and dried. Upon evaporation of the solvent, the desired compound is obtained.

Reduction of the compound carrying formyl group which is obtained above is performed by bringing the said compound into contact with a reducing agent in the presence of a solvent. There is no specific limitation on the reducing agent employed, so far as it is capable of reducing only formyl group into hydroxymethyl group without affecting other moieties of the compound. Preferred are an alkali metal hydride complex salt such as sodium borohydride, lithium aluminum hydride and potassium borohydride, and aluminum triisopropoxide. There likewise is no specific limitation on the solvent employed, so far as it does not participate in the reaction. In the case of using the alkali metal hydride complex salt, an alcohol such as methanol and ethanol and an ether such as ethyl ether, tetrahydrofuran and dioxane are preferred. In the case of using the aluminum tri-isopropoxide, isopropanol may be employed.

After completion of the reaction, the desired compound is recovered from the reaction mixture in the conventional manner. For instance after completion of the reaction, excess reagent is decomposed and extracted with an organic solvent such as n-hexane. The extract is washed and dried. Upon evaporation of the solvent, the desired compound is obtained.

The desired compound of the above general formula (II) produced as above may be converted to the corresponding salt with metals or organic bases as mentioned above in a conventional manner and can, if necessary, be further purified by the conventional method such as column chromatography and thin layer chromatography.

Process 2

The compound of the above general formula (I) wherein A is carboxyl group or an alkoxycarbonyl group and B is hydroxymethyl group, namely the compound of the general formula

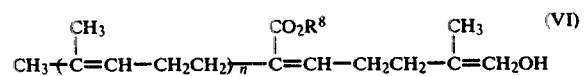

(wherein $R^8$ represents hydrogen atom or an alkyl group having 1 to 4 carbon atoms and n has the same meaning as above) can be produced by reacting a compound of the general formula

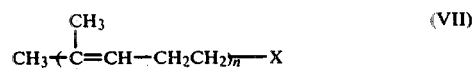

(wherein X represents chlorine, bromine or iodine and n has the same meaning as above) with a compound of the general formula

(wherein $R^9$ and $R^{11}$ may be the same or different and each represents an alkyl group having 1 to 4 carbon atoms) and a compound of the general formula

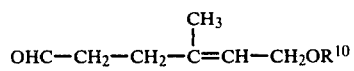

(IX)

(wherein $R^{10}$ is a protecting group for hydroxy group) in the presence of a base to form a compound of the general formula

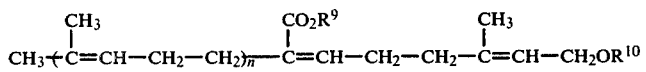

(X)

(wherein $R^9$, $R^{10}$ and n have the same meanings as above) and removing the protecting group for the hydroxy group from the so obtained compound and, if the corresponding carboxylic acid is required, hydrolyzing the ester compound.

In the present process, the condensation reaction involving the compound of the formula (VII), the compound of the formula (VIII) and the compound of the formula (IX) for preparing the compound of the formula (X) is carried out in the presence of a base and a solvent. There is no specific limitation on the base employed, so far as it belongs to the base adopted for the modified Wittig reaction [W. S. Wadsworth and W. D. Emmons, J. Am. Chem. Soc., Vol. 83, 1733 (1961)]. Preferred are an alkyllithium such as n-butyllithium and tert-butyllithium, a hydride of an alkali metal or an alkaline earth metal such as sodium hydride and calcium hydride, an alkali metal amide such as sodium amide and potassium amide, and an alkali metal alcoholate such as sodium methoxide, sodium ethoxide, potassium ethoxide and potassium tert-butoxide. There is no specific limitation on the solvent employed, so far as it does not participate in the reaction. Preferred are an ether such as ethyl ether, tetrahydrofuran and 1,2-dimethoxyethane, as aliphatic hydrocarbon such as n-pentane and n-hexane, a halogenated hydrocarbon such as methylene chloride, chloroform and ethylene dichloride, an aromatic hydrocarbon such as benzene and toluene, an aliphatic alcohol such as methanol, ethanol, n-propanol, isopropanol and tert-butanol, a dialkyl aliphatic acid amide such as dimethylformamide and diethylformamide, and dimethylsulfoxide. An appropriate solvent is chosen, in view of the base employed. There likewise is no specific limitation on the reaction temperature. Preferably the reaction is conducted at approximately 0°-70° C. in a stream of an inert gas such as nitrogen, helium and argon. The most preferable procedure is as follows: The compound of the formula (VIII) is dissolved in an organic solvent such as 1,2-dimethoxyethane, and, in a stream of an inert gas such as argon, to this solution is added at a temperature between 0° C. and room temperature a base such as sodium hydride and then added the compound of the formula (VII) at a temperature between room temperature and 50° C. Subsequently, the above-mentioned base is again added around 0° C., and the compound of the formula (IX) is then added at a temperature between room temperature and 50° C. The reaction period of time may vary depending mainly upon the sort of the base employed and the reaction temperature. Ordinarily, the period is between 2 and 5 hours.

After completion of the reaction, the desired compound of the formula (X) can be recovered from the reaction mixture in the conventional manner. For instance, after completion of the reaction ice-water is added to the reaction mixture and this is extracted with an organic solvent such as n-hexane. The organic solvent layer is washed and dried. Upon evaporation of the solvent, the desired compound is obtained. The desired compound thus obtained can, if necessary, be further purified by the conventional method such as column chromatography and thin layer chromatography.

The reaction for removing the protecting group for the hydroxy group of the compound having the above general formula (X) may vary depending upon the sort of the protecting group.

The reaction conditions and after-treatment are the same as mentioned in the above Process 1 and when the base is used as a reagent, simultaneous hydrolysis of the ester group may be effected.

The hydrolysis of the carboxylic acid ester compound of the above general formula (VI) (wherein $R^8$ is an alkyl group of 1 to 4 carbon atoms) obtained from the reaction for removing the protecting group for the hydroxy group may be effected according to the procedures for hydrolysis or alcoholysis of a conventional ester group in the presence of a base. As the base to be employed, preferable are an alkali metal or alkaline earth metal hydroxide such as sodium hydroxide, potassium hydroxide, barium hydroxide, an alkali metal carbonate such as sodium carbonate, potassium carbonate. The reaction can be preferably effected in the presence of water, an organic solvent such as an alcohol e.g. methanol, ethanol, n-propanol, an ether e.g. tetrahydrofuran, dioxane or a mixture of said organic solvent with water. There is no particular limitation on the reaction temperature, but the reaction is preferably effected between room temperature and around a boiling point of the solvent.

After completion of the reaction, the carboxylic acid derivative of the desired compounds having the above general formula (VI) may be recovered from the reaction mixture in a conventional manner and further converted to the corresponding metal or organic base salt as mentioned above. The desired compound having the above general formula (VI) obtained in the above process can, if necessary, be further purified by the conventional method such as column chromatography and thin layer chromatography.

Process 3

The compound of the above general formula (I) wherein A and B are the carbamoyl group as defined above can be produced by conversion of the carboxyl group or carboxylic acid ester group of the desired compound obtained by the aforesaid Processes 1 and 2 into the amide group.

In the process of this invention, the reaction is carried out by direct contact of the compound having carboxyl group or carboxylic acid ester group with an amine in the presence or absence of a solvent on conversion of the compound having carboxyl group into an intermediate commonly employable for amide synthesis such as acid chloride, acid anhydride or acid azide in the presence or absence of a solvent and subsequent contact with an amine. As the reagent for the intermediate to facilitate amidation, may be used dicyclohexyl carbodiimide, ethyl chlorocarbonate, p-toluenesulfonyl chloride, thionyl chloride, oxalyl chloride, diphenylphosphoric acid azide. There likewise is no specific limitation on the solvent employed, so far as it does not participate in the reaction. Preferred are an ether such as ethyl ether, tetrahydrofuran, dioxane and 1,2-dimethoxyethane, an aromatic hydrocarbon such as benzene, toluene, a halogenated hydrocarbon such as methylene chloride and chloroform, a carboxylic acid ester such as ethyl acetate. The reaction temperature is, in case of direct amidation, between room temperature and 150° C. and, in case of intermediate, between 0° C. and around room temperature. The reaction period may vary depending mainly upon the sort of the intermediate to be passed through and the reaction temperature, but ordinarily it is between 2 and 10 hours.

After completion of the reaction, the desired compound of the amidation reaction can be recovered from the reaction mixture in the conventional manner. For instance, after completion of the reaction, water is added to the reaction mixture and extraction is done with an organic solvent such as chloroform. The resulting organic solvent layer is washed with a dilute acid and a dilute alkali and dried. Upon evaporation of the solvent from the extract, the desired compound is obtained. The desired compound thus obtained can, if necessary, be further purified by the conventional method such as column chromatography and thin layer chromatography.

Process 4

The compound of the above general formula (I) wherein A or B is the aminomethyl group as defined above can be produced by reduction of the carbamoyl group in the end compound obtained in the above Process 3.

The reaction can be effected by bringing the compound having carbamoyl group into contact with a reducing agent in the presence of a solvent. As the reducing agent to be employed, there is no particular limitation so far as it can reduce carbamoyl group only into aminomethyl group without any influence on other portion of the compound. Preferred are an aluminum hydride compound such as aluminum hydride, lithium aluminum hydride, aluminum hydride diisobutoxide, lithium aluminum hydride bis(2-methoxyethoxide) and a borohydride compound such as sodium borohydride. As the solvent to be employed, preferred are an ether such as ethyl ether, tetrahydrofuran and an aromatic hydrocarbon such as benzene, toluene. There is no particular limitation on the reaction temperature and the reaction is preferably effected between −10° C. and around room temperature.

After completion of the reaction, the desired compound obtained through the reduction can be recovered from the reaction mixture in the conventional manner. For instance, after completion of the reaction, ethyl acetate is added to the reaction mixture to decompose an excess of the reducing agent, and the resulting precipitate is then filtered off. Upon evaporation of the solvent from the filtrate, the desired compound is obtained. The desired compound thus obtained can, if necessary, be further purified by the conventional method such as column chromatography and thin layer chromatography.

Process 5

The compound of the above general formula (I) wherein A is the mono-substituted aminomethyl group of those aminomethyl groups as defined above and B is hidroxymethyl group can be produced by reaction of a compound having the general formula

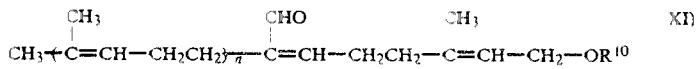

(wherein $R^{10}$ and n have the same meanings as above) with an amine compound followed by reduction of the Schiff's base thus obtained.

The reaction for producing Schiff's base from the compound of the above general formula (XI) is carried out in the presence of a solvent with or without an acid and/or a dehydrating agent. Preferable acid is an organic acid such as p-toluenesulfonic acid. As the solvent, preferable are an aromatic hydrocarbon such as benzene, toluene and a halogenated hydrocarbon such as dichloromethane, chloroform. There likewise is no specific limitation on the reaction temperature, but temperatures between room temperature and the reflux temperature of the solvent used are preferably adopted.

Reduction of the Schiff's base obtained above is performed by bringing the said compound into contact with a reducing agent in the presence of a solvent. There is no specific limitation on the reducing agent employed, so far as it is capable of reducing only $>C=N-$ group into aminomethyl group without affecting other moieties of the compound. Preferred are a borohydride compound such as sodium borohydride, lithium hydride, lithium hydride ethoxide and aluminum hydride diisobutoxide. As the solvent, it may depend upon the reducing agent applied, but an alcohol such as ethanol, propanol, an ether such as ethyl ether, tetrahydrofuran and an aromatic hydrocarbon such as benzene, toluene. There is no specific limitation on the reaction temperature, but temperatures between −10° C. and room temperature are preferably adopted.

In case the compound obtained by the reduction carries a remaining protecting group for the hydroxyl group, the desired compound can be obtained by removal of the remaining protecting group in the manner mentioned above in Process 1. The desired compound thus obtained can, if necessary, be further purified by the conventional method such as column chromatography and thin layer chromatography.

Process 6

The compound of the above general formula (I) wherein A and/or B are an acyloxymethyl or alkyloxymethyl group as defined above can be produced by acylating or alkylating the hydroxy group of the compound having hydroxymethyl group prepared in the above Processes 1 to 5 or of a compound having the general formula

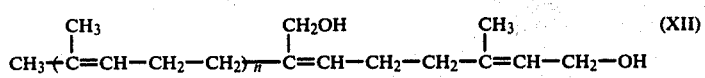

(XII)

(wherein n is as defined above).

In the present process, the reaction may be performed by bringing the compound carrying hydroxyl groups into contact with an acylating agent in the presence or absence of a solvent. There is no specific limitation on the acylating agent. employed, so fas as it belongs to one which is generally used for acylating a hydroxyl group. Preferred are an acid anhydride such as acetic anhydride, propionic anhydride, and succinic anhydride, glutaric anhydride, and an acid chloride such as acetyl chloride, acetyl bromide, butyryl chloride, isobutyryl chloride, benzoyl chloride, 2-thienylacetyl chloride, isonicotinoyl chloride, an inorganic acid salt with an organic base such as sulfuric anhydride pyridine reagent. Where the acid anhydride or acid halide is to be used as an acylating agent, the reaction is preferably carried out in the presence of a base. Such a base is exemplified by an organic base such as triethylamine, pyridine, picoline and lutidine, an inorganic base, for instance, an alkali metal hydroxide such as sodium hydroxide and potassium hydroxide and an alkali metal carbonate such as sodium carbonate and potassium carbonate, and an alkali metal salt of an organic acid such as sodium acetate and potassium acetate. For production of the compound having a heterocyclic aliphatic acyl group such as thiazolylthioacetyl, the acylation reaction is effected by using a halogenoaliphatic acid halide such as chloroacetyl chloride, bromoacetyl bromide and then the so obtained halogenoacylated product is reacted with a heterocyclic compound such as 2-mercapto-2-thiazoline in the presence of a base such as sodium hydride in a conventional manner. There is no specific limitation on the solvent which is optionally employed, so far as it does not participate in the reaction. Preferred are water, an ether such as ethyl ether, tetrahydrofuran and dioxane, a halogenated hydrocarbon such as methylene chloride and chloroform, an aromatic hydrocarbon such as benzene and toluene and a heterocyclic base such as pyridine and picoline. There likewise is no specific limitation on the reaction temperature but temperatures between 0° C. and 80° C. are preferably adopted. The reaction period of time may vary depending mainly upon the sort of the acylating agent and the reaction temperature. The period ordinarily is between 2 and 10 hours.

After completion of the reaction, the desired compound can be recovered from the reaction mixture in the conventional manner. For instance, after completion of the reaction, the reaction mixture is added to ice-water and extracted with an organic solvent such as ethyl ether. The organic solvent layer is washed and dried. Upon evaporation of the solvent from the extract, the desired compound is obtained. The desired compound thus obtained can be further purified, if necessary, by the conventional method such as column chromatography and thin layer chromatography. In case of inorganic acid or dibasic acid ester, the desired compound is converted to salts with metals or organic bases as mentioned above.

In the present process, the reaction may be performed by bringing the compound carrying hydroxy groups into contact with an alkylating agent in the presence or absence of a solvent. There is no specific limitation on the alkylating agent employed, so far as it belongs to one which is generally used for alkylating a hydroxyl group. Preferred are an alkyl halide and a dehydrohalogenating agent. The alkyl halide is exemplified by methyl chloride, methyl bromide, methyl iodide, ethyl iodide, n-propyl iodide, isopropyl iodide, n-butyl iodide, isobutyl iodide, hexyl iodide and octyl iodide. The dehydrohalogenating agent is exemplified by a metal oxide such as silver oxide, calcium oxide and barium oxide, a metal hydride such as sodium hydride and calcium hydride and a metal amide such as sodium amide and potassium amide. There is no specific limitation on the solvent which is optionally employed, so far as it does not participate in the reaction. Preferred are an ether such as tetrahydrofuran and dioxane, an aromatic hydrocarbon such as benzene and toluene, a dialkyl aliphatic acid amide such as dimethylformamide and dimethylacetamide, and dimethylsulfoxide. There likewise is no specific limitation on the reaction temperature, but temperatures around room temperature are preferably adopted. The reaction period of time varies depending mainly upon kind of the alkylating agent and the like. The period ordinarily is between 5 and 90 hours.

In the alkylating reaction, the compound having carboxyl group may simultaneously afford the esterified desired compound.

After completion of the reaction, the desired compound can be recovered from the reaction mixture in the conventional manner. For instance, after completion of the reaction, an excess of the alkyl halide is removed from the reaction mixture by evaporation. Water is added to the residue, and the resulting mixture is extracted with an organic solvent such as n-hexane. The organic solvent layer is washed and dried. Upon evaporation of the solvent, the desired compound is obtained. The desired compound thus obtained can be further purified, if necessary, by the conventional method such as column chromatography and thin layer chromatography.

The compounds of the above general formula (XI) and (XII) which may be used as a starting material in the above Processes 5 and 6 are all new substances and may be prepared, for example, according to the Process 1, except that a compound of the general formula

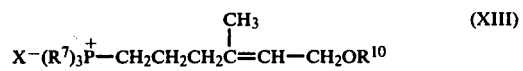

(XIII)

(wherein $R^7$ and $R^{10}$ are as defined above) is used as Wittig reagent instead of the compound (IV).

This invention will be more fully explained by way of the following examples and reference examples.

EXAMPLE 1

(E,Z,E) and (E,E,E)-7-hydroxymethyl-3,11,15-trimethyl-2,6,10,14-hexadecatetraenoic acid A suspension of 14.1 g of (E)-4-methyl-5-carboxy-4-penten-1-yltriphenylphosphonium bromide, 8.4 g of (E)-1,1-dimethoxy-6,10-dimethyl-5,9-undecadien-2-one and 2.5 g of 63.8% sodium hydride in 30 ml of anhydrous dimethyl sulfoxide was stirred at 50°–55° C. for 2.5 hours and 40 ml of acetic acid-water (5:1) was added thereto. The resulting mixture was again stirred at 50°–55° C. for 30 minutes. After completion of the reaction, the reaction mixture was extracted four times with n-hexane and the extracts were washed with water, dried over anhydrous sodium sulfate and then the solvent was distilled off to leave 10.4 g of an yellow oily substance. The resulting oil was dissolved in 50 ml of ethanol, 1.2 g of sodium borohydride was added thereto at 5°–10° C. and the resulting mixture was stirred for 1 hour. To the reaction mixture were added ethyl ether and water and, after stirring, an aqueous layer was separated and neutralized with hydrochloric acid under ice-cooling. The so separated oily substance was extracted with ether and the extract was washed with water and dried over anhydrous sodium sulfate. The solvent was distilled off to afford 3.98 g of the end product.

NMR spectrum δ ppm (CDCl$_3$): 1.56 (6H, singlet), 1.67 (3H, singlet), 1.96 (3H, singlet), 1.8–2.4 (12H, multiplet), 4.01, 4.11 (2H, singlet respectively), 4.9–5.5 (3H, multiplet), 5.67 (1H, singlet)

IR spectrum ν cm$^{-1}$ (liquid film): 3600-2400, 1695, 1640, 1440, 1375, 1240.

EXAMPLE 2

(E,Z,E), (E,E,E), (Z,Z,E) and (Z,E,E)-7-hydroxymethyl-3,11,15-trimethyl-2,6,10,14-hexadecatetraenoic acid Reaction of 23.5 g of (E) and (Z)-4-methyl-5-carboxy-4-penten-1-yltriphenylphosphonium bromide, 12.7 g of (E)-1,1-dimethoxy-6,10-dimethyl-5,9-undecadien-2-one and 4.2 g of 63.8% sodium borohydride in 50 ml of anhydrous dimethyl sulfoxide was effected in accordance with the process of Example 1 and thereafter reduction with 2.0 g of sodium borohydride in 70 ml of ethanol was effected to afford 6.50 g of the end product.

NMR spectrum δ ppm (CDCl$_3$): 1.56 (6H, singlet), 1.67 (3H, singlet), 1.80, 1.96 (3H, singlet respectively), 1.8–2.4 (12H, multiplet), 4.01, 4.11 (2H, singlet respectively), 4.9–5.5 (3H, multiplet), 5.67 (1H, singlet)

IR spectrum ν cm$^{-1}$ (liquid film): 3600-2400, 1695, 1640, 1440, 1375, 1240

EXAMPLE 3

(E,Z,E) and (E,E,E)-7-ethoxycarbonyl-3,11,15-trimethyl-2,6,10,14-hexadecatetraen-1-ol To a suspension of 0.75 g of 63.8% sodium hydride in 30 ml of dimethoxyethane was added dropwise a solution of 4.5 g of triethyl phosphonoacetate in 5 ml of dimethoxyethane at room temperature and the resulting mixture was stirred for 30 minutes. Further, 5.6 g of homogeranyl iodide was added and the mixture was stirred at 50° C. for 1 hour. The reaction mixture was cooled to 5° C. and then 0.75 g of sodium hydride was added and stirring was done for 1 hour. 3.4 g of (E)-6-acetoxy-4-methyl-4-heptenal was added dropwise and reaction was conducted at 50° C. for 1 hour. To the reaction mixture was added water and the mixture was extracted with n-hexane. The hexane layer was washed with water, dried over anhydrous sodium sulfate and the solvent was distilled off. The so obtained oily substance was purified by a silica gel column chromatography to yield 4.7 g of (E,Z,E) and (E,E,E)-7-ethoxycarbonyl-3,11,15-trimethyl-2,6,10,14-hexadecatetraen-1-ol acetate.

1.3 g of the acetate thus obtained was dissolved in methanol and 10 ml of a 5% aqueous sodium hydroxide-methanol solution was added. The mixture was left at room temperature overnight. After completion of the reaction, water was added and extraction was conducted with n-hexane. The hexane layer was washed with water, dried and the solvent was distilled off. The resulting residue was purified by a silica gel (30 g) chromatography to yield 850 mg of the end product.

NMR spectrum δ ppm (CCl$_4$): 1.22 (3H, triplet), 1.51 (6H, singlet), 1.61 (6H, singlet), 1.9–2.5 (12H, multiplet), 3.95 (2H, doublet), 4.08 (2H, quartet), 5.0–5.4 (3H, multiplet), 5.71, 6.85 (1H, triplet respectively)

IR spectrum ν cm$^{-1}$ (liquid film): 3450, 1710, 1642, 1375, 1265, 1200, 1185, 1105, 1090, 1060, 1020.

EXAMPLE 4

(E,Z,E) and (E,E,E)-7-carboxy-3,11,15-trimethyl-2,6,10,14-hexadecatetraen-1-ol

To a solution of 1.0 g of the (E,Z,E) and (E,E,E)-7-ethoxycarbonyl-3,11,15-trimethyl-2,6,10,14-hexadecatetraen-1-ol acetate obtained in the process of Example 3 in 20 ml of methanol was added 10 ml of a 5% aqueous sodium hydroxide-methanol solution and the mixture was heated under reflux for 7 hours. After completion of the reaction, the reaction mixture was made acidic with hydrochloric acid and extracted with ethyl ether. The ether layer was washed with water, dried and the solvent was distilled off. The resulting oily substance was purified by a silica gel (15 g) column chromatography to yield 700 mg of the end product.

NMR spectrum δ ppm (CDCl$_3$): 1.54 (6H, singlet), 1.65 (6H, singlet), 1.9–2.6 (12H, multiplet), 4.05 (2H, doublet), 5.04 (2H, multiplet), 5.40 (1H, doublet), 6.49 (1H, broad singlet)

IR spectrum ν cm$^{-1}$ (liquid film): 3300, 1700, 1640, 1390, 1220, 1160, 1050, 1030, 970, 900, 755

EXAMPLE 5

(E,Z,E) and (E,E,E)-7-hydroxymethyl-3,11,15-trimethyl-2,6,10,14-hexadecatetraenamide To a solution of 400 mg of (E,Z,E) and (E,E,E)-7-hydroxymethyl-3,11,15-trimethyl-2,6,10,14-hexadecatetraenoic acid in 10 ml of anhydrous dichloromethane were added 0.15 ml of triethylamine and then 0.17 ml of ethyl chlorocarbonate at 0° C. and stirring was effected for 30 minutes. To the reaction mixture was introduced dry ammonia gas for 20 minutes and thereafter stirring was continued for 30 minutes. To the reaction mixture was added water and extracted with ethyl ether. The ether layer was washed with aqueous sodium hydrogencarbonate and then with water and dried over anhydrous sodium sulfate. The solvent was distilled off and the residue was separated by a thin-layer chromatography using a silica gel to afford 191 mg of the end product and 110 mg of the starting carboxylic acid.

NMR spectrum δ ppm (CDCl$_3$): 1.60 (6H, singlet), 1.65 (3H, singlet), 1.97 (3H, singlet), 1.9–2.4 (12H, multiplet), 4.00, 4.10 (2H, singlet, respectively), 4.9–5.6 (3H, multiplet), 5.63 (1H, singlet).

IR spectrum ν cm$^{-1}$ (liquid film): 3320, 3180, 1670, 1640, 1605, 1440, 1370, 1305, 1000.

EXAMPLE 6

(E,E) and (Z,E)-N,N-diethyl-8-hydroxy-3,7-dimethyl-2,6-octadienamide

Following the same manner as in Example 5, the reaction and after-treatment were conducted by using 1.0 g of (E,E) and (Z,E)-8-hydroxy-3,7-dimethyl-2,6-octadienoic acid, 0.9 ml of triethylamine, 0.62 ml of ethyl chlorocarbonate and 0.67 ml of diethylamine in 20 ml of dichloromethane to afford 850 mg of the end product.

NMR spectrum δ ppm (CDCl$_3$): 1.10 (6H, triplet), 1.61 (3H, singlet), 1.84 (3H, singlet), 2.1–2.3 (4H, multiplet), 3.1–3.5 (4H, multiplet), 3.90 (2H, singlet), 5.1–5.5 (1H, multiplet), 5.74 (1H, singlet).

IR spectrum ν cm$^{-1}$ (liquid film): 3400, 1650, 1610, 1440, 1380, 1365, 1270, 1220, 1140, 1075, 1020.

EXAMPLE 7

4-[(E,E) and (Z,E)-8-hydroxy-3,7-dimethyl-2,6-octadienoyl]-morpholine

Following the same manner as in Example 5, the reaction and after-treatment were conducted by using 1.0 g of (E,E) and (Z,E)-8-hydroxy-3,7-dimethyl-2,6-octadienoic acid, 0.9 ml of triethylamine, 0.62 ml of ethyl chlorocarbonate and 0.60 ml of morpholine in 20 ml of dichloromethane to afford 800 mg of the end product.

NMR spectrum δ ppm (CDCl$_3$): 1.64 (3H, singlet), 1.85 (3H, singlet), 2.1–2.4 (4H, multiplet), 3.58 (8H, singlet), 3.92 (2H, singlet), 5.1–5.5 (1H, multiplet), 5.70 (1H, singlet)

EXAMPLE 8

1-[(E,E) and (Z,E)-8-hydroxy-3,7-dimethyl-2,6-octadienoyl]-4-(3,4-methylenedioxybenzyl)piperazine Following the same manner as in Example 5, the reaction and after-treatment were conducted by using 3.0 g of (E,E) and (Z,E)-8-hydroxy-3,7-dimethyl-2,6-octadienoic acid, 3.0 ml of triethylamine, 2.1 g of ethyl chlorocarbonate and 2.7 g of 1-(3,4-methylenedioxybenzyl)piperazine in 40 ml of dichloromethane to afford 2.7 g of the end product.

NMR spectrum δ ppm (CDCl$_3$): 1.58 (3H, singlet), 1.75 (3H, singlet), 2.0–2.5 (8H, multiplet), 3.41 (2H, singlet), 3.3–3.7 (4H, multiplet), 3.86 (2H, singlet), 5.1–5.5 (1H, multiplet), 5.65 (1H, singlet), 5.88 (2H, singlet), 6.68, 6.80 (3H)

IR spectrum ν cm$^{-1}$ (liquid film): 3400, 1610, 1490, 1440, 1240, 1035, 1000, 930.

EXAMPLE 9

(E,Z,E) and (E,E,E)-N-benzyl-7-hydroxymethyl-3,11,15-trimethyl-2,6,10,14-hexadecatetraenamide To a solution of 1.0 g of (E,Z,E) and (E,E,E)-7-hydroxymethyl-3,11,15-trimethyl-2,6,10,14-hexadecatetraenoic acid in 10 ml of ethyl acetate were added 0.41 ml of benzylamine, 0.84 ml of diphenylphosphoric acid azide and then 0.5 ml of triethylamine under ice-cooling and the reaction mixture was stirred at room temperature for 5 hours. After completion of the reaction, the reaction mixture was diluted with ethyl ether, washed successively with dilute hydrochloric acid, aqueous sodium hydrogencarbonate and water and dried over anhydrous sodium sulfate. The solvent was distilled off to give an oily substance, which was then purified by a column chromatography using silica gel (25 g) to afford 960 mg of the end product.

NMR spectrum δ ppm (CDCl$_3$): 1.56 (6H, singlet), 1.65 (3H, singlet), 1.97 (3H, singlet), 1.9–2.3 (12H, multiplet), 3.95 (2H, broad singlet), 4.86 (2H, doublet), 4.8–5.2 (3H, multiplet), 5.54 (1H, singlet), 7.18 (5H, singlet)

IR spectrum ν cm$^{-1}$ (liquid film): 3300, 1660, 1630, 1540, 1500, 1245, 1175

EXAMPLE 10

(E,Z,E), (E,E,E), (Z,Z,E) and (Z,E,E)-N-ethyl-7-hydroxymethyl-3,11,15-trimethyl-2,6,10,14-hexadecatetraenamide Following the same manner as in Example 9, the reaction and after-treatment were conducted by using 1.1 g of (E,Z,E), (E,E,E), (Z,Z,E) and (Z,E,E)-7-hydroxymethyl-3,11,15-trimethyl-2,6,10,14-hexadecatetraenoic acid, 350 mg of ethylamine hydrochloride, 0.80 ml of diphenylphosphoric acid azide and 1.0 ml of triethylamine in 6.0 ml of N,N-dimethylformamide to afford 780 mg of the end product.

NMR spectrum δ ppm (CDCl$_3$): 1.12 (3H, triplet), 1.58 (6H, singlet), 1.66 (3H, singlet), 1.81, 1.97 (3H, singlet respectively), 1.9–2.4 (12H, multiplet), 3.28 (2H, multiplet), 4.00 4.10 (2H, singlet respectively), 4.9–5.4 (3H, multiplet), 5.55 (1H, singlet)

IR spectrum ν cm$^{-1}$ (liquid film): 3300, 1660, 1630, 1550, 1260, 1010

EXAMPLE 11

(E,Z,E), (E,E,E), (Z,Z,E) and (Z,E,E)-N-(2-pyrrolidinoethyl)-7-hydroxymethyl-3,11,15-trimethyl-2,6,10,14-hexadecatetraenamide Following the same manner as in Example 9, the reaction was conducted using 1.0 g of (E,Z,E), (E,E,E), (Z,Z,E) and (Z,E,E)-7-hydroxymethyl-3,11,15-trimethyl-2,6,10,14-hexadecatetraenoic acid and 450 mg of 1-(2-aminoethyl)pyrrolidine in 6.0 ml of N,N-dimethylformamide and the reaction mixture was extracted with chloroform. The chloroform layer was washed with aqueous sodium hydrogencarbonate and extracted with dilute hydrochloric acid. The hydrochloric acid layer was neutralized with sodium hydrogencarbonate and extracted with chloroform. The chloroform layer was washed with water, dried and the solvent was distilled off. The residue was purified by a column chromatography using alumina (20 g) to afford 1.0 g of the end product.

NMR spectrum δ ppm (CDCl$_3$): 1.56 (6H, singlet), 1.65 (3H, singlet), 1.80, 1.96 (3H, singlet respectively), 1.4–1.9 (4H, multiplet), 1.9–2.3 (12H, multiplet), 2.3–2.8 (4H, multiplet), 3.0–3.5 (4H, multiplet), 3.95, 4.05 (2H, singlet respectively), 4.9–5.5 (3H, multiplet), 5.65 (1H, singlet)

IR spectrum ν cm$^{-1}$ (liquid film): 3400, 1665, 1630, 1540, 1255, 1185, 925

EXAMPLE 12

(E,Z,E) and (E,E,E)-N-(p-methylphenyl)-7-acetoxymethyl-3,11,15-trimethyl-2,6,10,14-hexadecatetraenamide A mixture of 850 mg of (E,Z,E) and (E,E,E)-7-hydroxymethyl-3,11,15-trimethyl-2,6,10,14-hexadecatetraenoic acid acetate prepared from the corresponding free acid in a conventional manner and 2.0 ml of oxalyl chloride was left at room temperature overnight. The reaction mixture was concentrated under reduced pressure and the residue was dissolved in 5 ml of anhydrous ethyl ether and 600 mg of p-toluidine was added under ice-cooling. The reaction mixture was left at room temperature for 3 hours and then diluted with ether and filtered. The ether layer was washed with aqueous sodium hydrogencarbonate and then with dilute hydrochloric acid. After washing with water and drying, the solvent was distilled off to afford 600 mg of the end product.

NMR spectrum $\delta$ ppm (CDCl$_3$): 1.55 (6H, singlet), 1.63 (3H, singlet), 2.00 (3H, singlet), 2.16 (3H, singlet), 2.34 (3H, singlet), 1.9–2.5 (12H, multiplet), 4.43; 4.57 (2H, singlet respectively), 4.8–5.5 (3H, multiplet), 5.67 (1H, singlet), 7.22 (4H, quartet).

IR spectrum $\nu$ cm$^{-1}$ (liquid film): 1740, 1660, 1640, 1600, 1529, 1230, 1020

EXAMPLE 13

1-[(E,Z,E), (E,E,E), (Z,Z,E) and (Z,E,E)-7-hydroxymethyl-3,11,15-trimethyl-2,6,10,14-hexadecatetraenoyl]pyrrolidine Following the same manner as in Example 9, the reaction and after-treatment were conducted by using 1.1 g of (E,Z,E), (E,E,E), (Z,Z,E) and (Z,E,E)-7-hydroxymethyl-3,11,15-trimethyl-2,6,10,14-hexadecatetraenoic acid, 0.36 ml of pyrrolidine and 0.97 ml of diphenylphosphoric acid azide in 6 ml of N,N-dimethylformamide to afford 820 mg of the end product.

NMR spectrum $\delta$ ppm (CDCl$_3$): 1.60 (6H, singlet), 1.65 (3H, singlet), 1.86 (3H, singlet), 1.4–2.7 (16H, multiplet), 3.2–4.7 (4H, multiplet), 4.4–5.5 (3H, multiplet), 5.23 (1H, singlet)

IR spectrum $\nu$ cm$^{-1}$ (liquid film): 3400, 1655, 1610, 1450, 1380, 1350, 1020, 840

EXAMPLE 14

4-[(E,E,E)-7-hydroxymethyl-3,11,15-trimethyl-2,6,10,14-hexadecatetraenoyl]morpholine Following the same manner as in Example 5, the reaction and after-treatment were conducted by using 400 mg of (E,E,E)-7-hydroxymethyl-3,11,15-trimethyl-2,6,10,14-hexadecatetraenoic acid, 0.16 ml of triethylamine, 0.13 ml of ethyl chlorocarbonate and 0.20 ml of morpholine in 10 ml of dichloromethane to afford 210 mg of the end product.

NMR spectrum $\delta$ ppm (CDCl$_3$): 1.56 (6H, singlet), 1.61 (3H, singlet), 1.80 (3H, singlet), 1.9–2.5 (12H, multiplet), 3.53 (8H, singlet), 3.94 (2H, singlet), 4.8–5.5 (3H, multiplet), 5.65 (1H, singlet)

IR spectrum $\nu$ cm$^{-1}$ (liquid film): 3430, 1650, 1610, 1440, 1270, 1240, 1120

EXAMPLE 15

1-[(E,Z,E), (E,E,E), (Z,Z,E) and (Z,E,E)-7-hydroxymethyl-3,11,15-trimethyl-2,6,10,14-hexadecatetraenoyl]-4-(2-hydroxyethyl)piperazine Following the same manner as in Example 9, the reaction and after-treatment were conducted by using 1.1 g of (E,Z,E), (E,E,E), (Z,Z,E) and (Z,E,E)-7-hydroxymethyl-3,11,15-trimethyl-2,6,10,14-hexadecatetraenoic acid, 460 mg of 1-(2-hydroxyethyl)piperazine and 0.80 ml of diphenylphosphoric acid azide in 6 ml of N,N-dimethylformamide to afford 870 mg of the end product.

NMR spectrum $\delta$ ppm (CDCl$_3$): 1.58 (6H, singlet), 1.65 (3H, singlet), 1.82, 1.96 (3H, singlet respectively), 1.9–2.3 (12H, multiplet), 2.3–2.7 (6H, multiplet), 3.3–3.8 (6H, multiplet), 3.90, 4.05 (2H, singlet respectively), 4.9–5.4 (3H, multiplet), 5.70 (1H, singlet)

IR spectrum $\nu$ cm$^{-1}$ (liquid film): 3500, 1650, 1610, 1380, 1240, 1190, 1150

EXAMPLE 16

1-[(E,Z,E) and (E,E,E)-7-hydroxymethyl-3,11,15-trimethyl-2,6,10,14-hexadecatetraenoyl]-4-phenylpiperazine Following the same manner as in Example 9, the reaction and after-treatment were conducted by using 1.0 g of (E,Z,E) and (E,E,E)-7-hydroxymethyl-3,11,15-trimethyl-2,6,10,14-hexadecatetraenoic acid, 700 mg of 1-phenylpiperazine and 0.75 ml of diphenylphosphoric acid azide in 6 ml of N,N-dimethylformamide to afford 900 mg of the end product.

NMR spectrum $\delta$ ppm (CDCl$_3$): 1.57 (6H, singlet), 1.65 (3H, singlet), 1.85 (3H, singlet), 1.9–2.4 (12H, multiplet), 2.9–3.2 (4H, multiplet), 3.4–3.9 (4H, multiplet), 3.98, 4.05 (2H, singlet respectively), 4.9–5.5 (3H, multiplet), 5.75 (1H, singlet), 6.6–7.4 (5H, multiplet)

IR spectrum $\nu$ cm$^{-1}$ (liquid film): 3430, 1655, 1620, 1600, 1505, 1500, 1440, 1380, 1340, 1280, 1230, 1180, 1160, 1025, 760

EXAMPLE 17

(E,Z,E) and (E,E,E)-N,N-diethyl-7-acetoxymethyl-3,11,15-trimethyl-2,6,10,14-hexadecatetraenamide Following the same manner as in Example 12, 1.0 g of (E,Z,E) and (E,E,E)-7-acetoxymethyl-3,11,15-trimethyl-2,6,10,14-hexadecatetraenoic acid was converted to the corresponding acid chloride with 1.5 ml of oxalyl chloride and the reaction with 1.0 ml of diethylamine afforded 820 mg of the end product.

NMR spectrum $\delta$ ppm (CDCl$_3$): 1.12 (6H, triplet), 1.58 (6H, singlet), 1.64 (3H, singlet), 1.90 (3H, singlet), 2.00 (3H, singlet), 1.9–2.4 (12H, multiplet), 3.38 (4H, quartet), 4.44, 4.56 (2H, singlet respectively), 4.8–5.5 (3H, multiplet), 5.77 (1H, singlet)

IR spectrum $\nu$ cm$^{-1}$ (liquid film): 1745, 1655, 1630, 1450, 1435, 1380, 1270, 1230, 1135, 1015

EXAMPLE 18

1-[(E,Z,E) and (E,E,E)-7-hydroxymethyl-3,11,15-trimethyl-2,6,10,14-hexadecatetraenoyl]-4-(3,4-methylenedioxybenzyl)-piperazine Following the same manner as in Example 5, the reaction and after-treatment were conducted by using 1.2 g of (E,Z,E) and (E,E,E)-7-hydroxymethyl-3,11,15-trimethyl-2,6,10,14-hexadecatetraenoic acid, 0.53 ml of triethylamine, 0.47 ml of ethyl chlorocarbonate and 1.2 g of 1-(3,4-methylenedioxybenzyl)piperazine in 30 ml of dichloromethane to afford 830 mg of the end product.

NMR spectrum δ ppm (CDCl$_3$): 1.50 (6H, singlet), 1.58 (3H, singlet), 1.74 (3H, singlet), 1.8–2.5 (16H, multiplet), 2.46 (1H, singlet), 3.31 (2H, singlet), 3.2–3.7 (4H, multiplet), 3.90, 3.98 (2H, singlet respectively), 4.8–5.5 (3H, multiplet), 5.66 (1H, singlet), 5.86 (2H, singlet), 6.69 (2H, singlet), 6.80 (1H, singlet)

IR spectrum ν cm$^{-1}$ (liquid film): 3400, 1650, 1610, 1600, 1490, 1440, 1370, 1240, 1040, 1000

EXAMPLE 19

1-[(E,Z,E) and (E,E,E)-7-hydroxymethyl-3,11,15-trimethyl-2,6,10,14-hexadecatetraen-1-yl]-4-phenylpiperazine A solution of 213 mg of 1-[(E,Z,E) and (E,E,E)-7-hydroxymethyl-3,11,15-trimethyl-2,6,10,14-hexadecatetraenoyl]-4-phenylpyrazine produced in the above Example 16 in 5 ml of anhydrous ethyl ether was added dropwise at 0° C. to a solution of aluminum hydride prepared from 70 mg of lithium aluminum hydride and 80 mg of aluminum chloride in 10 ml of anhydrous ethyl ether. Stirring was continued at 0° C. for 30 minutes and then 5% sulfuric acid was added and then the mixture was stirred. The aqueous layer was separated, neutralized with a 5% aqueous sodium hydroxide solution and extracted with ether. The ether layer was washed with water and dried and then the solvent was distilled off to afford 120 mg of the end product.

NMR spectrum δ ppm (CDCl$_3$): 1.50 (6H, singlet), 1.53 (6H, singlet), 1.8–2.3 (12H, multiplet), 2.3–2.7 (4H, multiplet), 3.91, 3.99 (2H, singlet respectively), 4.8–5.4 (4H, multiplet), 6.5–7.3 (5H, multiplet)

IR spectrum ν cm$^{-1}$ (liquid film): 3300, 1670, 1600: 1580, 1500, 1450, 1380, 1230, 1140, 1000.

EXAMPLE 20

1-[(E,Z,E) and (E,E,E)-7-hydroxymethyl-3,11,15-trimethyl-2,6,10,14-hexadecatetraen-1-yl]-4-(3,4-methylenedioxybenzyl)-piperazine A solution of 820 mg of 1-[(E,Z,E) and (E,E,E)-7-hydroxymethyl-3,11,15-trimethyl-2,6,10,14-hexadecatetraenoyl]-4-(3,4-methylenedioxybenzyl)piperazine produced in the above Example 18 in 10 ml of anhydrous ethyl ether was subjected to reduction with aluminum hydride prepared from 450 mg of lithium aluminum hydride and 520 mg of aluminum chloride in 20 ml of anhydrous ethyl ether according to the procedures of Example 19 and then after-treatment was conducted to afford 780 mg of the end product.

NMR spectrum δ ppm (CDCl$_3$): 1.59 (9H, singlet), 1.64 (3H, singlet), 1.9–2.3 (12H, multiplet), 2.42 (8H, singlet), 2.96 (2H, doublet), 3.36 (2H, singlet), 3.43, 4.05 (2H, singlet respectively), 4.9–5.6 (4H, multiplet), 5.91 (2H, singlet), 6.81 (3H, multiplet)

IR spectrum ν cm$^{-1}$ (liquid film): 3370, 3200, 1670, 1610, 1500, 1490, 1440, 1370, 1330, 1240, 1130, 1035, 1000.

EXAMPLE 21

1-[(E,E) and (E,Z)-8-hydroxy-3,7-dimethyl-2,6-octadien-1-yl]-4-(3,4-methylenedioxybenzyl)piperazine A solution of 1.0 g of 1-[(E,E) and (E,Z)-8-hydroxy-3,7-dimethyl-2,6-octadienoyl]-4-(3,4-methylenedioxybenzyl)-piperazine produced in the above Example 8 in 10 ml of anhydrous ethyl ether was subjected to reduction with aluminum hydride prepared from 1.0 g of lithium aluminum hydride and 1.3 g of aluminum chloride in 30 ml of anhydrous ethyl ether according to the procedures of Example 19 and after-treatment was conducted to afford 0.9 g of the end product.

NMR spectrum δ ppm (CDCl$_3$): 1.60 (6H, singlet), 2.0–2.3 (4H, multiplet), 2.45 (8H, sinlet), 2.95 (2H, doublet), 3.36 (2H, singlet), 3.90 (2H, sinlet), 5.1–5.5 (1H, multiplet), 5.88 (2H, singlet), 6.68, 6.80 (3H)

IR spectrum ν cm$^{-1}$ (liquid film): 3300, 1485, 1440, 1240, 1130, 1035, 1000, 925, 800.

EXAMPLE 22

(E,Z,E) and (E,E,E)-7-benzylcarbamoyl-3,11,15-trimethyl-2,6,10,14-hexadecatetraen-1-ol 660 mg of (E,Z,E) and (E,E,E)-7-carboxy-3,11,15-trimethyl-2,6,10,14-hexadecatetraen-1-ol was dissolved in 10 ml of dichloromethane. The solution was cooled to 0° C., 440 mg of dicyclohexylcarbodiimide was added and the mixture was stirred for 1 hour. Then, 0.5 ml of benzylamine was added and stirring was continued for 1 hour. The reaction mixture was left at room temperature overnight and water was added followed by extraction with ethyl ether. The oily substance derived from the extract was purified by a thin-layer chromatography to afford 315 mg of the end product.

NMR spectrum δ ppm (CDCl$_3$): 1.56 (6H, singlet), 1.65 (6H, singlet), 1.9–2.4 (12H, multiplet), 4.07 (2H, doublet), 4.44 (2H, doublet), 4.9–5.3 (3H, multiplet), 5.39, 6.39 (1H, triplet respectively), 7.25 (5H, singlet)

IR spectrum ν cm$^{-1}$ (liquid film): 3320, 1660, 1620, 1530, 1455, 1430, 1250, 1000.

EXAMPLE 23

(E,Z,E) and (E,E,E)-7-isobutylaminomethyl-3,11,15-trimethyl-2,6,10,14-hexadecatetraen-1-ol To a solution of 400 mg of (E,Z,E) and (E,E,E)-7-formyl-3,11,15-trimethyl-2,6,10,14-hexadecatetraen-1-ol tetraydropyranyl ether in 5 ml of anhydrous benzene were added 0.3 ml of isobutylamine, 10 mg of p-toluenesulfonic acid and 1 g of Molecular Sieve (5A) and the resulting mixture was left at room temperature for 3 days. The reaction mixture was filtered and the benzene layer was washed with aqueous sodium carbonate and then dried over anhydrous sodium sulfate. The solvent was distilled off to leave a Schiff's base, which was then dissolved in 7 ml of ethanol and 25mg of sodium borohydride was added and the resulting mixture was stirred for 1 hour. Excess reagent was decomposed with dilute hydrochloric acid and water was added followed by extraction with ethyl ether. The amine derived from the ether layer was dissolved in 10 ml of methanol, hydrochloric acid was added until it became acidic and the mixture was left at room temperature overnight. After the methanol was distilled off and water was added, the mixture was made alkaline with sodium hydroxide and extracted with ethyl ether. The ether layer was washed with water, dried and the solvent was distilled off to afford 400 mg of the end product.

NMR spectrum δ ppm (CDCl$_3$): 0.84 (6H, doublet), 1.54 (6H, singlet), 1.62 (6H, singlet), 3.10 (2H, broad singlet), 3.35 (2H, singlet), 4.10 (2H, doublet), 4.9–5.3 (4H, multiplet)

IR spectrum ν cm$^{-1}$ (liquid film): 3400, 1670, 1380, 1110, 1070, 1020, 830

EXAMPLE 24

(E,Z,E) and (E,E,E)-7-(3-piperidinopropylaminomethyl)-3,11,15-trimethyl-2,6,10,14-hexadecatetraen-1-ol The Schiff's base produced from 700 mg of (E,Z,E) and (E,E,E)-7-formyl-3,11,15-trimethyl-2,6,10,14-hexadecatetraen-1-ol tetrahydropyranyl ether and 500 mg of 3-piperidinopropylamine according to Example 23 was reduced with 37 mg of sodium borohydride and then the tetrahydropyranyl group was removed by the addition of hydrochloric acid in methanol to afford 650 mg of the end product.

NMR spectrum δppm (CDCl$_3$): 1.55 (6H, singlet), 1.65 (6H, singlet), 3.2–3.5 (4H, multiplet), 3.34 (2H, singlet), 4.10 (2H, doublet), 5.0–5.4 (4H, multiplet)

IR spectrum ν cm$^{-1}$ (liquid film): 3450–3250, 1665, 1375, 1350, 1305, 1250, 1180, 1150, 1120, 1070, 1015, 990.

EXAMPLE 25

(E,Z), (E,E), (Z,Z) and (Z,E)-7-octylaminomethyl-3,11-dimethyl-2,6,10-dodecatrien-1-ol Following the same manner as in Example 23, 1.0 g of (E,Z), (E,E), (Z,Z) and (Z,E)-7-formyl-3,11-dimethyl-2,6,10-dodecatrien-1-ol tetrahydropyranyl ether was subjected to reaction with 1.0 g of n-octylamine to give a Schiff's base. The base was reduced with 100 mg of sodium borohydride and then the protective group was removed with hydrochloric acid-methanol to afford 1.3 g of the end product.

NMR spectrum δ ppm (CDCl$_3$): 0.79 (3H, triplet), 1.19 (12H, broad singlet), 1.51 (3H, inglet), 1.58 (6H, singlet), 3.06 (2H, broad singlet), 3.30 (2H, singlet), 4.02 (2H, doublet), 5.0–5.4 (4H, multiplet)

IR spectrum ν cm$^{-1}$ (liquid film): 3300, 1670, 1380, 1120, 1080, 1065, 1035, 1020, 900, 720

EXAMPLE 26

(E,E)-8-acetoxy-2,6-dimethyl-2,6-octadienyl-1-ol sulfate pyridine salt

To a solution of 1.0 g of (E,E)-8-acetoxy-2,6-dimethyl-2,6-octadien-1-ol in 20 ml of anhydrous benzene was added 3.0 g of anhydrous sulfuric acid-pyridine reagent and the mixture was heated and stirred at 60° C. for 3 hours. After completion of the reaction, the reaction mixture was washed with n-hexane and then with benzene-hexane (1:1). The resulting oily substance was dissolved in chloroform and insoluble substance was filtered off. The chloroform layer was concentrated to afford 1.8 g of the end product.

NMR spectrum δ ppm (CDCl$_3$): 1.62 (6H, singlet), 2.00 (3H, singlet), 1.9–2.3 (4H, multiplet), 4.40 (2H, singlet), 4.50 (2H, doublet), 5.0–5.3 (2H, multiplet), 8.0–9.2 (5H, multiplet).

IR spectrum ν cm$^{-1}$ (liquid film): 1740, 1550, 1240, 1200, 1060, 1040, 960, 760, 690

EXAMPLE 27

(E,E)-8-acetoxy-2,6-dimethyl-2,6-octadienyl-1-ol sulfate sodium salt

To a solution of 3.4 g of 8-acetoxy-2,6-dimethyl-2,6-octadienyl-1-ol sulfate pyridine salt in 20 ml of ethyl acetate was added dropwise at room temperature 7 ml of a solution of sodium 2-ethylhexanoate in ethyl acetate (2 mM/ml). White precipitate thus formed was centrifuged, washed with ethyl acetate-ethyl ether (1:1) and dried. The end product thus obtained was 2.4 g as white crystals.

NMR spectrum δ ppm (D$_2$O): 1.64 (6H, singlet), 2.01 (3H, singlet), 1.9–2.3 (4H, multiplet), 4.35 (2H, singlet), 4.50 (2H, doublet), 5.1–5.6 (2H, multiplet).

IR spectrum ν cm$^{-1}$ (Nujol): 1745, 1470, 1385, 1255, 1210, 1080, 1025, 940, 880, 835

EXAMPLE 28

(E,Z,E) and (E,E,E)-7-hydroxymethyl-3,11,15-trimethyl-2,6,10,14-hexadecatetraen-ol disulfate pyridine salt Following the same manner as in Example 26, the reaction was conducted with 3.0 g of (E,Z,E) and (E,E,E)-7-hydroxymethyl-3,11,15-trimethyl-2,6,10,14-hexadecatetraen-1-ol and 5.0 g of anhydrous sulfuric acid-pyridine reagent in anhydrous benzene and after-treatment was conducted to afford 4.4 g of the end product.

NMR spectrum δ ppm (CDCl$_3$): 1.56, 1.63 (12H, singlet respectively), 1.7–2.3 (12H, multiplet), 4.5 (2H, doublet), 4.55 (2H, singlet), 4.8–5.5 (4H, multiplet), 7.9–9.1 (10H, multiplet)

IR spectrum ν cm$^{-1}$ (liquid film): 1640, 1620, 1545, 1490, 1250, 1195, 1050, 960, 750, 680

EXAMPLE 29

(E,Z,E) and (E,E,E)-7-hydroxymethyl-3,11,15-trimethyl-2,6,10,14-hexadecatetraen-1-ol disulfate sodium salt Following the procedures of Example 27, a solution of 2.2 g of (E,Z,E) and (E,E,E)-7-hydroxymethyl-3,11,15-trimethyl-2,6,10,14-hexadecatetraen-1-ol disulfate pyridine salt prepared in Example 28 in 20 ml of ethyl acetate was treated with 6.0 ml (2 mM/ml) of sodium 2-ethylhexanoate to afford 1.4 g of the end product as a white powder.

NMR spectrum δ ppm (D$_2$O): 1.54, 1.60 (12H, singlet respectively), 1.8–2.3 (12H, multiplet), 4.5 (4H, multiplet), 4.9–5.4 (4H, multiplet)

IR spectrum ν cm$^{-1}$ (Nujol film): 1465, 1380, 1250, 1210, 1140, 1080, 960

EXAMPLE 30

(E,Z,E) and (E,E,E)-7-hydroxymethyl-3,11,15-trimethyl-2,6,10,14-hexadecatetraen-1-ol disuccinate sodium salt To a solution of 1.0 g of (E,Z,E) and (E,E,E)-7-hydroxymethyl-3,11,15-trimethyl-2,6,10,14-hexadecatetraen-1-ol in 20 ml of anhydrous benzene were added 1.0 g of succinic anhydride and 3.0 ml of pyridine and the mixture was boiled under reflux for 5 hours. After completion of the reaction, the reaction mixture was diluted with benzene and extracted with an aqueous 5% sodium hydroxide. The extract was washed with benzene, made acidic with dilute hydrochloric acid and extracted with ethyl ether. The ether layer was washed with water, dried over anhydrous sodium sulfate and the solvent was distilled off to give 1.4 g of the corresponding carboxylic acid. 1.3 g of the so obtained carboxylic acid was dissolved in 5 ml of anhydrous tetrahydrofuran. The solution was added dropwise under stirring and ice-cooling to a suspension of 260 mg of 50% sodium hydride in 5 ml of anhydrous tetrahydrofuran. After stirring for 1 hours, anhydrous ethyl ether was added. The so formed precipitate was recovered by filtration, washed with ethyl ether and dried to afford 1.4 g of the end product.

NMR spectrum δ ppm ($D_2O$): 1.52, 1.60 (12H, singlet respectively), 1.8–2.3 (12H, multiplet), 2.46 (8H, singlet), 4.4–4.7 (4H, multiplet), 4.9–5.5 (4H, multiplet)

IR spectrum ν $cm^{-1}$ (Nujol): 1740, 1580, 1460, 1380, 1250, 1165

EXAMPLE 31

(E,Z,E) and (E,E,E)-7-hydroxymethyl-3,11,15-trimethyl-2,6,10,14-hexadecatetraen-1-ol bis-2-thienylacetate To a solution of 1.0 g of (E,Z,E) and (E,E,E)-7-hydroxymethyl-3,11,15-trimethyl-2,6,10,14-hexadecatetraen-1-ol in 5 ml of anhydrous pyridine was added dropwise 2 ml of 2-thienylacetyl chloride under ice-cooling. After 1 hour, ice-water was added and extraction was done with ethyl ether. The ether layer was washed successively with dilute hydrochloric acid, aqueous sodium hydrogencarbonate and water and dried over anhydrous sodium sulfate. The solvent was distilled off to give an oily substance, which was then purified by a column chromatography with silica gel (15 g) to afford 1.1 g of the end product.

NMR spectrum δ ppm ($CDCl_3$): 1.60, 1.65 (12H, singlet respectively), 1.9–2.3 (12H, multiplet), 3.77 (4H, singlet), 4.56 (2H, doublet), 4.62 (2H, singlet), 4.9–5.5 (4H, multiplet), 6.8–7.4 (6H, multiplet).

IR spectrum ν $cm^{-1}$ (liquid film): 1770, 1740, 1615, 1545, 1440, 1320, 1260, 1220, 1160, 1105, 850.

EXAMPLE 32

(E,Z,E) and (E,E,E)-7-hydroxymethyl-3,11,15-trimethyl-2,6,10,14-hexadecatetraen-1-ol diisonicotinate To a solution of 1.0 g of (E,Z,E) and (E,E,E)-7-hydroxymethyl-3,11,15-trimethyl-2,6,10,14-hexadecatetraen-1-ol in 30 ml of anhydrous chloroform was added 3.0 ml of triethylamine and then 2.0 g of isonicotinoyl chloride hydrochloride dropwise at room temperature. Stirring was continued for 3 hours. The reaction mixture was poured into ice-water, extracted with chloroform, washed with aqueous sodium hydrogencarbonate and water and dried over anhydrous sodium sulfate. The solvent was distilled off to give an oily substance, which was then purified by a column chromatography with silica gel (20 g) to afford 1.4 g of the end product.

NMR spectrum δ ppm ($CDCl_3$): 1.58, 1.66, 1.80 (12H, singlet respectively), 1.9–2.4 (12H, multiplet), 4.85 (2H, doublet), 4.90 (2H, singlet), 4.9–5.6 (4H, multiplet), 7.80 (4H, multiplet), 8.80 (4H, multiplet)

IR spectrum ν $cm^{-1}$ (liquid film): 1725, 1600, 1565, 1410, 1325, 1275, 1120, 1060, 935

EXAMPLE 33

(E,Z,E) and (E,E,E)-7-hydroxymethyl-3,11,15-trimethyl-2,6,10,14-hexadecatetraen-1-ol bis-2-thiazolin-2-yl thioacetate To a solution of 3.0 g of (E,Z,E) and (E,E,E)-7-hydroxymethyl-3,11,15-trimethyl-2,6,10,14-hexadecatetraen-1-ol in 30 ml of ethyl ether were added 1.75 ml of pyridine and then 10 ml of a solution of 1.7 ml of chloroacetyl chloride in anhydrous ethyl ether dropwise under ice-cooling. After stirring under ice-cooling for 1 hour, ice-water was added and the mixture was extracted with ether. The ether layer was washed with aqueous sodium hydrogencarbonate and then water and dried over anhydrous sodium sulfate. The solvent was distilled off to give 3.8 g of the bis-chloroacetate.

To a suspension of 220 mg of 50% sodium hydride in 20 ml of anhydrous tetrahydrofuran was added dropwise a solution of 520 mg of 2-mercapto-2-thiazoline in 10 ml of tetrahydrofuran with stirring at room temperature. After stirring for 30 minutes, a solution of 920 mg of the bis-chloroacetate produced as above in 5 ml of tetrahydrofuran and 50 mg of sodium iodide were added and the resulting mixture was heated at 50° C. and stirred for 4 hours. After completion of the reaction, ice-water was added to the reaction mixture and extraction was done with ethyl ether. The ether layer was washed with aqueous sodium hydrogencarbonate and water and dried over anhydrous sodium sulfate. The solvent was distilled off to give an oily substance, which was then purified by a column chromatography with silica gel (15 g) to afford 1.1 g of the end product.

NMR spectrum δ ppm ($CDCl_3$): 1.60, 1.70, (12H, singlet), 1.9–2.4 (12H, multiplet), 3.40 (4H, triplet), 3.90 (4H, singlet), 4.20 (4H, triplet), 4.62 (2H, doublet), 4.68 (2H, singlet), 4.9–5.5 (4H, multiplet).

IR spectrum ν $cm^{-1}$ (liquid film): 1735, 1575, 1450, 1380, 1285, 1260, 1150, 990, 960, 920.

REFERENCE EXAMPLE (E,Z,E) and (E,E,E)-7-hydroxymethyl-3,11,15-trimethyl-2,6,10,14-hexadecatetraen-1-ol a.

(E)-1,1-dimethoxy-6,10-dimethyl-5,9-undecadien-2-one

To a solution of 17.4 g of metalic sodium in 350 ml of absolute ethanol was added dropwise 160 g of methyl 4,4-dimethoxyacetoacetate with stirring at room temperature. After 1 hour, geranyl bromide produced from 130 g of geraniol was added dropwise under ice-cooling. The mixture was left at room temperature overnight and then refluxed for 1 hour. To the reaction mixture was added a solution of 42 g of sodium hydroxide in 1.4 l of ethanol and 1180 ml of water and the mixture was heated under reflux for 6 hours. The n-hexane extract was distilled under reduced pressure to afford 134 g of the end product.

bp 92°–95° C./0.05 mmHg

NMR spectrum δ ppm ($CDCl_3$): 1.58 (6H, singlet), 1.62 (3H, singlet), 1.8–2.7 (8H, multiplet), 3.35 (6H, singlet), 4.39 (1H, singlet), 5.05 (2H, multiplet)

IR spectrum ν $cm^{-1}$ (liquid film): 1735, 1075, 1000 b. (E,Z,E) and (E,E,E)-7-hydroxymethyl-3,11,15-trimethyl-2,6,10,14-hexadecatetraen-1-ol To a suspension of 58.6 g of (E)-triphenyl-4-methyl-6-(2'-tetrahydropyranyloxy)-4-hexenyl phosphonium iodide in 300 ml of anhydrous tetrahydrofuran was added dropwise under nitrogen stream at −20° C. a 1 mole equivalent solution of n-butyllithium in hexane. After stirring at −20° C. for 1 hour, a solution of 25.4 g of (E)-1,1-dimethoxy-6,10-dimethyl-5,9-undecadien-2-one in 50 ml of anhydrous tetrahydrofuran was added. After stirring at room temperature for 3 hours, icewater was added to the reaction mixture and extraction was done with n-hexane. The resulting oily substance was suspended in 300 ml of 5% acetic acid without further purification and stirred at room temperature for 2 hours. From the n-hexane extract was obtained 28.0 g of (E,Z,E) and (E,E,E)-7-formyl-3,11,15-trimethyl-2,6,10,14-hexadecatetraen-1-ol tetrahydropyranyl ether. The compound was dissolved in 200 ml of ethanol, 1.5 g of sodium borohydride was added and stirring was made for 2 hours. This was treated with dilute acetic acid, water was added and extraction was done with n-hexane. The product was dissolved in 200 ml of methanol and 200 mg of p-toluenesulfonic acid was added. The mixture was left at room temperature overnight and neutralized with aqueous sodium hydrogencarbonate. The methanol was distilled off and extraction was done with ether. The so obtained oily substance was purified by a column chromatography to afford 18.2 g of a mixture of (E,Z,E) (E,E,E) isomers of the desired 7-hydroxymethyl-3,11,15-trimethyl-2,6,10,14-hexadecatetraen-1-ol.

NMR spectrum $\delta$ ppm (CDCl$_4$): 1.58 (6H, singlet), 1.66 (6H, singlet), 1.9–2.3 (12H, multiplet), 3.94 (2H, singlet), 3.97 (2H, doublet), 5.0–5.3 (4H, multiplet)

IR spectrum $\nu$ cm$^{-1}$ (liquid film)k: 3300, 1665, 1440, 1380, 1000, 840

What is claimed is:

1. 7-Hydroxymethyl-3,11,15-trimethyl-2,6,10,14-hexadecatetraenoic acid.
2. 7-Carboxy-3,11,15-trimethyl-2,6,10,14-hexadecatetraen-1-ol.
3. 7-Ethoxycarbonyl-3,11,15-trimethyl-2,6,10,14-hexadecatetraen-1-ol.

* * * * *

UNITED STATES PATENT AND TRADEMARK OFFICE
CERTIFICATE OF CORRECTION

PATENT NO.   : 4,199,519     Page 1 of 2
DATED        : April 22, 1980
INVENTOR(S)  : HIROSHI MISHIMA et al It is certified that error appears in the above-identified patent and that said Letters Patent are hereby corrected as shown below:

Abstract, line 11: rewrite "akyl" as ---alkyl---.

Column 2, line 22: before "alkali", replace "a" with ---an---.

Column 2, line 22: replace "or" with ---an---.

Column 6, line 36: replace "hexadecatetraen-1-B1" with ---hexadecatetraen-1-ol---.

Column 13, line 37: before "aliphatic", replace "as" with ---an---.

Column 23, line 29: replace "1529" with ---1520---.

Column 26, lines 17 and 18: replace "sinlet" (two occurrences) with ---singlet---.

Column 27, line 45: replace "inglet" with ---singlet---.

Column 28, line 24: replace "hexadecatetraen-ol" with ---hexadecatetraen-1-ol---.

UNITED STATES PATENT AND TRADEMARK OFFICE
CERTIFICATE OF CORRECTION

PATENT NO. : 4,199,519
DATED : April 22, 1980
INVENTOR(S) : HIROSHI MISHIMA et al It is certified that error appears in the above–identified patent and that said Letters Patent are hereby corrected as shown below:

Column 32, line 11: replace "$(CDCl_4)$" with ---$(CCl_4)$---.

Signed and Sealed this

Twenty-ninth Day of July 1980

[SEAL]

*Attest:*

SIDNEY A. DIAMOND

*Attesting Officer*  *Commissioner of Patents and Trademarks*